United States Patent
Nan et al.

(10) Patent No.: US 11,098,071 B2
(45) Date of Patent: Aug. 24, 2021

(54) GPR84 RECEPTOR ANTAGONIST AND USE THEREOF

(71) Applicant: SHANGHAI INSTITUTE OF MATERIA MEDICA, CHINESE ACADEMY OF SCIENCES, Shanghai (CN)

(72) Inventors: Fajun Nan, Shanghai (CN); Xin Xie, Shanghai (CN); Linhai Chen, Shanghai (CN); Qing Zhang, Shanghai (CN); Yufeng Xiao, Shanghai (CN); Hui Yang, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/490,837

(22) PCT Filed: Feb. 28, 2018

(86) PCT No.: PCT/CN2018/077584
§ 371 (c)(1),
(2) Date: Sep. 3, 2019

(87) PCT Pub. No.: WO2018/161831
PCT Pub. Date: Sep. 13, 2018

(65) Prior Publication Data
US 2020/0010492 A1    Jan. 9, 2020

(30) Foreign Application Priority Data
Mar. 6, 2017    (CN) .......................... 201710128201.3

(51) Int. Cl.
| C07F 9/09 | (2006.01) |
| C07F 9/655 | (2006.01) |
| C07F 9/6553 | (2006.01) |
| C07F 9/6561 | (2006.01) |

(52) U.S. Cl.
CPC .............. *C07F 9/09* (2013.01); *C07F 9/6561* (2013.01); *C07F 9/65517* (2013.01); *C07F 9/65539* (2013.01)

(58) Field of Classification Search
CPC .............................. C07F 9/09; C07F 9/65517
USPC ........................................................ 546/175
See application file for complete search history.

(56) References Cited

FOREIGN PATENT DOCUMENTS

| CN | 103998448 A | 8/2014 |
| CN | 104870445 A | 8/2015 |
| WO | 2013/092791 A1 | 6/2013 |
| WO | WO-2013092791 A1 * | 6/2013 | ............. A61P 31/00 |
| WO | 2014/095798 A1 | 6/2014 |
| WO | WO-2014095798 A1 * | 6/2014 | ............. A61P 11/00 |

OTHER PUBLICATIONS

Caplus English abstract DN 17:23032, reduction products of hydroxyanthraquinones. John Hall et al. (Year: 1923).*
STNext genus search. (Year: 2020).*
International Search Report in PCT Appln. PCT/CN2018/077584 dated Sep. 13, 2018; 6 pages.
Gulland, J.M. et al.; "The Constitution of Yeast Ribonucleic Acid. Part XI. Synthesis of Uridine-2' Phosphate"; *Journal of the Chemical Society*; Jan. 1, 1947; pp. 338-342.
Dupont, S. et al.; "P031 GPR84 inhibition as a novel therapeutic approach in IBD: mechanistic and translational studies"; *J.Crohns Colitis*; 2015; 9; S92-3.
Vanhoutte, F. et al.; "P612 Human safety, pharmacokinetics and pharmacodynamics of the GPR84 antagonist GLPG1205, a potential new approach to treat IBD"; *J.Crohns Colitis*; 2015; 9; S387-S387.
Wittenberger, T. et al.; "An Expressed Sequence Tag (EST) Data Mining Strategy Succeeding in the Discovery of New G-Protein Coupled Receptors"; *J. Mol. Biol.*; vol. 307; 2001; pp. 799-813.
Mitsunobu, N. et al.; "Photolyses of Derivatives of Naphthyl and Anthryl Phosphates and Methylphosphonates," *Bull. Chem. Soc. Jpn.*; 1995; vol. 68; No. 11; pp. 3189-3197.

* cited by examiner

*Primary Examiner* — Rita J Desai
(74) *Attorney, Agent, or Firm* — Kilpatrick Townsend & Stockton LLP

(57) ABSTRACT

The present invention relates to a GPR84 receptor antagonist and use thereof. The GPR84 receptor antagonist of the present invention has a structure as represented by formula (I), the definitions of R1, R2, R3, R4, $L_1$, $L_2$, $L_3$, $L_4$, $L_5$, $L_6$, Y, Z, and rings A, B, C, and D are as described in the description and claims. The GPR84 receptor antagonist of the present invention can competitively inhibit the activation of the receptor caused by an agonist of GPR84, and can be used in the preparation of a medicament for treating related diseases caused by high expression or high excitability of GPR84 receptor, the diseases including multiple sclerosis, inflammatory bowel disease, arthritis and the like.

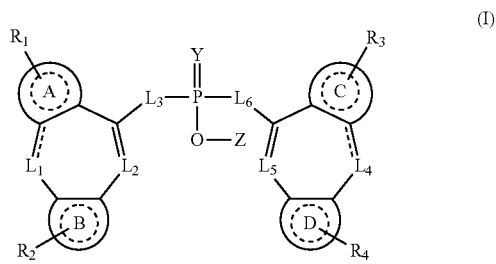

11 Claims, No Drawings

GPR84 RECEPTOR ANTAGONIST AND USE THEREOF

CROSS-REFERENCES TO RELATED APPLICATIONS

This application is a national phase application under 35 U.S.C. 371 claiming priority to PCT/CN2018/077584, filed Feb. 28, 2018, which application claims priority to CN 201710128201.3, filed Mar. 6, 2017, the teachings of which are hereby incorporated by reference in their entireties for all purposes.

TECHNICAL FIELD

The present invention relates to a ligand molecule of G protein-coupled receptor 84 (GPR84). The ligand molecule of the present invention has an antagonistic activity of GPR84, can competitively inhibit the activation of the receptor by an agonist of GPR84, and can be used for the treatment of a related disease caused by hyper-excitability or high expression of GPR84 receptor, such as multiple sclerosis, inflammatory bowel disease, arthritis and the like.

BACKGROUND TECHNIQUE

GPR84 (G protein-coupled receptor 84) is a medium-chain fatty acid (C9-C14) receptor firstly discovered by Wittenberger et al. in 2001 (*J. Mol. Biol.* 2001, 307, 799-813), and it is mainly expressed in bone marrow, peripheral blood leukocytes (including neutrophils, eosinophils, basophils) and adipocytes. In the presence of lipopolysaccharide (LPS), GPR84 expression is up-regulated in monocytes/macrophages, and medium-chain fatty acids can significantly up-regulate the expression of IL-12 p40 subunit in macrophage cell line RAW264.7 by GPR84, regulate immune response of Th1 cells, promote the occurrence of inflammation and play an important role in the development of inflammatory diseases such as multiple sclerosis (MS), inflammatory bowel disease, arthritis and the like. Moreover, the occurrence of metabolic diseases such as obesity, diabetes and the like is closely related to chronic inflammation. When macrophages invade adipose tissue, the occurrence of inflammation can be promoted by the secretion of cytokines, and GPR84 expression in adipocytes will be increased, indicating that GPR84 is also involved in cross-regulation between fatty acid metabolism and the immune system.

Since GPR84 can promote the occurrence of inflammation, it plays an important role in the development of inflammation-related diseases. Therefore, an inflammation-related disease such as multiple sclerosis, inflammatory bowel disease, arthritis and the like can be treated by inhibiting the activity of GPR84 by GPR84 antagonist.

To date, GPR84 antagonist is only reported in two patent documents from Belgian Galapagos Company (WO 2013/092791; WO 2014/095798). Both of these patent documents show that all of such antagonists have a structural nucleus of dihydropyrimidine isoquinolinone. In December of the same year, the company reported that the GPR84 antagonist GLPG1205 (structure not published) at an oral dose of 3 mg/kg/d can obviously relieve the symptoms of enteritis in inflammatory bowel disease (IBD) model of a mouse induced by dextran sulphate sodium (DSS) and the effect is similar to the clinically positive drugs cyclosporin (20 mg/kg/d) and sulfazalazine (25 mg/kg/d). (*J Crohns Colitis* 2015, 9 Suppl 1, S387; *J Crohns Colitis* 2015, 9 Suppl 1, S92-3). The Phase I clinical trial of GLPG1205 was completed a year ago, but the company reported at the end of January 2016 that there was no significant difference between GLPG1205 and placebo in the treatment of inflammatory bowel disease in Phase IIa clinical trials and announced the failure of the clinical trials. The specific results will be announced in the second half of this year. It is possible to develop GLPG1205 as a therapeutic drug for other indications.

The failure of clinical trial of GLPG1205 is likely due to the defect in the activity or drug-likeness of the compound itself. GPR84 is still an effective target for targeted therapy of inflammatory diseases. Although the current research on GPR84 is still relatively preliminary, and its detailed pathological function and its role in immune regulation remain still need to be further elucidated, the discovery of GPR84 antagonist with high activity and high selectivity will continue to promote the researches and developments of function of the receptor, target validation and drugs targeting the receptor.

SUMMARY OF THE INVENTION

The object of the present invention is to provide a novel GPR84 antagonist, a process preparation and use thereof.

The first aspect of the invention provides a compound or a pharmaceutically acceptable salt having the structure of formula I,

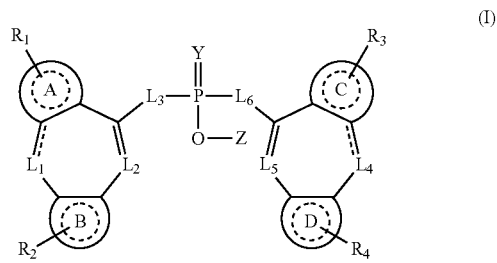

wherein, Y is O or S; Z is H, or an ion of the following metal: $L_1$, Na, K, Ca, Mg, Cu, Fe, Zn, Al, Mn, or a conjugated acid of the following base: $NH_3$, arginine, betaine, caffeine, choline, N,N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, glucosamine, aminoglucose, histidine, hydroxycobalamin, isopropylamine, lysine, methyl glucosamine, morpholine, piperazine, piperidine, polyamine resin, procaine, purine, theobromine, triethylamine, trimethylamine, tripropylamine, trometamol and the like;

$L_3$ and $L_6$ are each independently O, S, NH or $CH_2$;

each of rings A, B, C, and D is independently a $C_6$-$C_{10}$ aromatic ring, a $C_3$-$C_{10}$ cycloalkane ring, a $C_3$-$C_{10}$ heterocycloalkane ring, or a $C_3$-$C_{10}$ heteroaryl ring;

$R_1$, $R_2$, $R_3$, and $R_4$ are each independently 1 to 4 substituents on rings A, B, C, and D, and each substituent is independently absent, hydroxyl, mercapto, amino, F, Cl, Br, I, —$C_rH_{2r}$-$L_7$-$C_sH_{2s+1}$, —$C_rH_{2r}$—N($C_tH_{2t+1}$)—$C_sH_{2s+1}$, substituted or unsubstituted $C_1$-$C_6$ alkyl, substituted or unsubstituted $C_3$-$C_6$ cycloalkyl, substituted or unsubstituted $C_6$-$C_{10}$ aryl, substituted or unsubstituted $C_3$-$C_{10}$ heteroaryl, the above substitution means that there is one or more substituents selected from the group consisting of $C_1$-$C_6$ alkyl, $C_1$-$C_6$ alkoxy, halogen, hydroxyl, amino, —COO$C_1$-$C_6$ alkyl, —COOH; $L_7$ is each independently O, S, NH, each r is independently an integer of 0-6, each s is independently an integer of 0-6, and each t is independently an integer of 1-6;

$L_2$ and $L_5$ are each independently absent, CH, N;

$L_1$ and $L_4$ are each independently absent, CH, O, S, SO, $SO_2$, —CH═CH—, CO, —C(═$CH_2$)—, substituted or unsubstituted $C_1$-$C_6$ alkylidene, —NH—, —N($C_1$-$C_4$ alkyl)-, $C_3$-$C_6$ cycloalkyl or $C_3$-$C_6$ heterocycloalkyl, said "substituted" means that there is one or more substituents selected from the group consisting of $C_1$-$C_6$ alkyl, $C_1$-$C_6$ alkoxy, halogen, hydroxy; ══ represents a single bond or a double bond.

In another preferred embodiment, each of rings A, B, C and D is independently a benzene ring, a $C_3$-$C_6$ cycloalkane ring, a $C_3$-$C_6$ heterocycloalkane ring or a $C_3$-$C_6$ heteroaryl ring.

In another preferred embodiment, each of rings A, B, C and D is independently a benzene ring, a thiophene ring, a furan ring, a pyridine ring, a pyrimidine ring, an oxazole ring, a thiazole ring, a pyrazole ring, a pyrrole ring, a furan ring, a cyclohexane ring, a cyclopentane ring or a cycloheptane ring.

In another preferred embodiment, $R_1$, $R_2$, $R_3$ and $R_4$ are each independently one, two or three substituents on rings A, B, C and D, and each substituent is independently absent, substituted or unsubstituted $C_1$-$C_4$ alkyl, —$C_rH_{2r}$-$L_7$-$C_sH_{2s+1}$, —$C_rH_{2r}$—N($C_tH_{2t+1}$)—$C_sH_{2s+1}$, hydroxyl, mercapto, amino, F, Cl, Br, I; the above substitution means there is one or more substituents selected from the group consisting of halogen, hydroxyl, amino, —COO$C_1$-$C_6$ alkyl, —COOH; $L_7$ is each independently O, S, NH, each r is independently an integer of 0-4, each s is independently an integer of 0-4, and each t is independently an integer of 1-4.

In another preferred embodiment, $L_1$ and $L_4$ are each independently absent, CH, O, S, SO, $SO_2$, —CH═CH—, CO, —C(═$CH_2$)—, substituted or unsubstituted $C_1$-$C_4$ alkylidene, —NH—, —N($C_1$-$C_3$ alkyl)-, $C_3$-$C_6$ cycloalkyl or $C_3$-$C_6$ oxa-cycloalkyl, said substitution means there is one or more substituents selected from the group consisting of $C_1$-$C_6$ alkyl, $C_1$-$C_6$ alkoxy, halogen, hydroxyl.

In another preferred embodiment, the $C_3$-$C_6$ oxa-cycloalkyl is —C(dioxolane)-.

In another preferred embodiment, a carbon attached to $L_3$ and/or $L_6$ and a carbon of ring B and/or ring D form —CH═CH— when $L_2$ and/or $L_5$ are absent.

In another preferred embodiment, a carbon attached to $L_3$ and/or $L_6$ and a carbon attached to $L_2$ and/or $L_5$ form —CH═CH— or —CH═N— when $L_2$ and/or $L_5$ are CH or N.

In another preferred embodiment, $R_1$ represents 1-2 substituents on ring A, and each substituent is independently absent, —O($C_1$-$C_4$)alkyl, hydroxy, F, Cl, Br, I, $C_1$-$C_4$ alkyl, $C_1$-$C_4$ haloalkyl, —$C_2H_4$COOH, —$C_2H_4$COO$C_2H_5$.

In another preferred embodiment, $R_2$ represents 1-2 substituents on ring B, and each substituent is independently absent, —O($C_1$-$C_4$)alkyl, hydroxy, F, Cl, Br, I, $C_1$-$C_4$ alkyl, $C_1$-$C_4$ haloalkyl, —$C_2H_4$COOH, —$C_2H_4$COO$C_2H_5$.

In another preferred embodiment, $R_3$ represents 1-2 substituents on ring C, and each substituent is independently absent, —O($C_1$-$C_4$)alkyl, hydroxy, F, Cl, Br, I, $C_1$-$C_4$ alkyl, $C_1$-$C_4$ haloalkyl, —$C_2H_4$COOH, —$C_2H_4$COO$C_2H_5$.

In another preferred embodiment, $R_4$ represents 1-2 substituents on ring D, and each substituent is independently absent, —O($C_1$-$C_4$)alkyl, hydroxy, F, Cl, Br, I, $C_1$-$C_4$ alkyl, $C_1$-$C_4$ haloalkyl, —$C_2H_4$COOH, —$C_2H_4$COO$C_2H_5$.

In another preferred embodiment, $L_1$ is absent, CH, $CH_2$, O, —N($C_1$-$C_2$ alkyl)-, S, —CH═CH—, —C(═$CH_2$)—, —C(═O)—, —CH($CH_3$)—, —$CH_2CH_2$—, —C($CH_2CH_2$)—, —S(═O)—, —$SO_2$— or —C(—O$CH_2CH_2$O—)—.

In another preferred embodiment, $L_4$ is absent, CH, $CH_2$, O, —N($C_1$-$C_2$ alkyl)-, S, —CH═CH—, —C(═$CH_2$)—, —C(═O)—, —CH($CH_3$)—, —$CH_2CH_2$—, —C($CH_2CH_2$)—, —S(═O)—, —$SO_2$— or —C(—O$CH_2CH_2$O—)—.

In another preferred embodiment, when $L_2$ is absent, a carbon attached to $L_3$ and a carbon of ring B form —CH═CH—.

In another preferred embodiment, when $L_5$ is absent, a carbon attached to $L_6$ and a carbon of ring D form —CH═CH—.

In another preferred embodiment, a carbon attached to $L_3$ and $L_2$ form —CH═CH— or —CH═N— when $L_2$ is CH or N.

In another preferred embodiment, a carbon attached to $L_6$ and $L_5$ form —CH═CH— or —CH═N— when $L_5$ is CH or N.

In another preferred embodiment, the compound is:

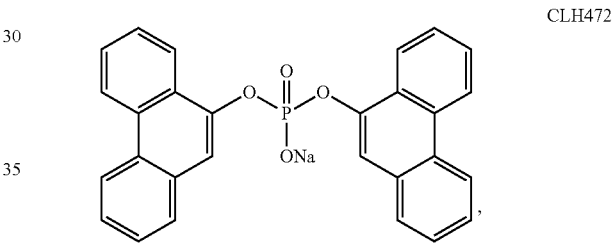

CLH472

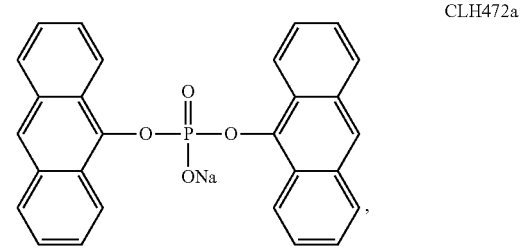

CLH472a

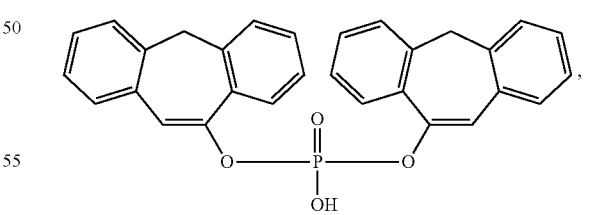

CLH478

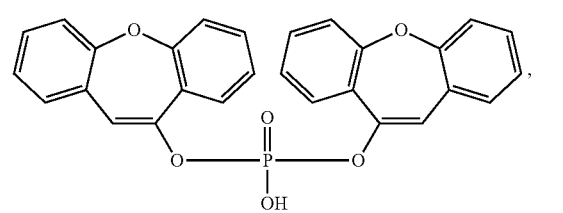

CLH482

CLH508
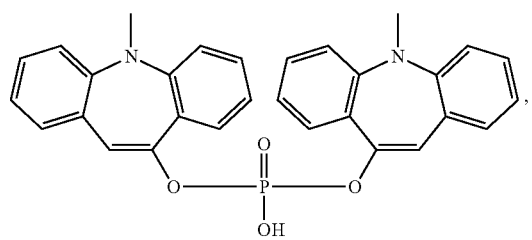
CLH514
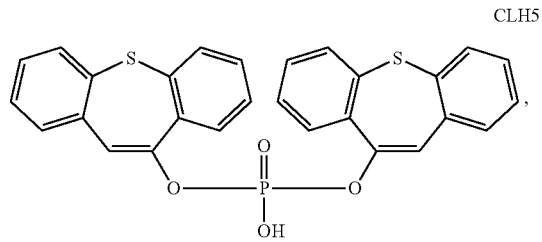
CLH524
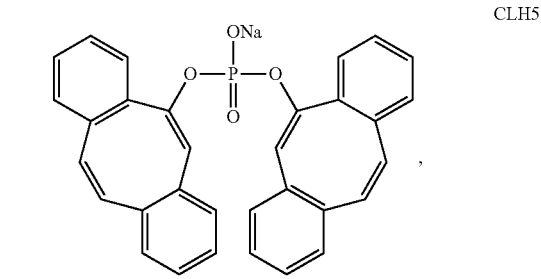
CLH524a
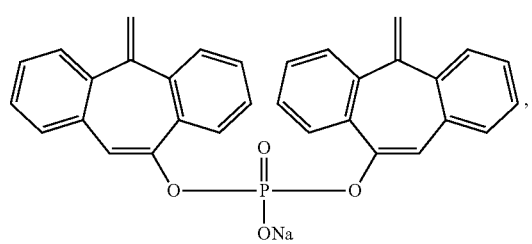
CLH528
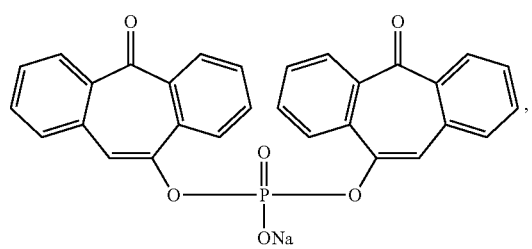
CLH528a
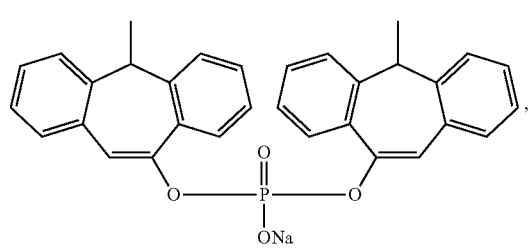
XYF528
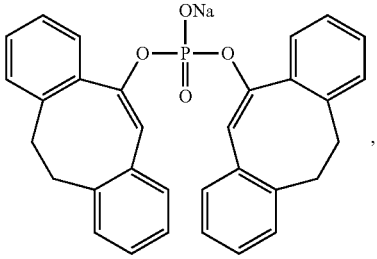
XYF532
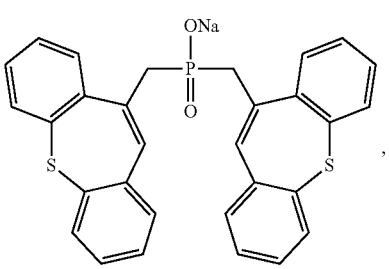
CLH536
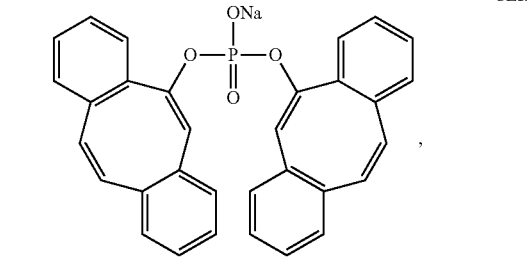
CLH544
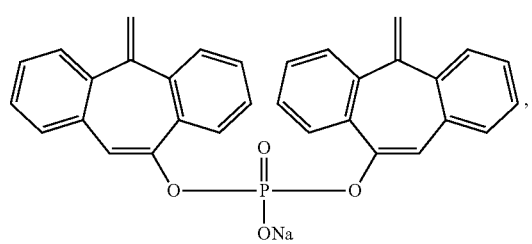
CLH544a
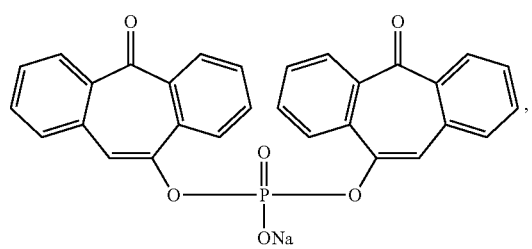
CLH548
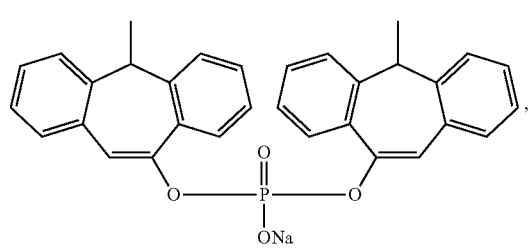

CLH552
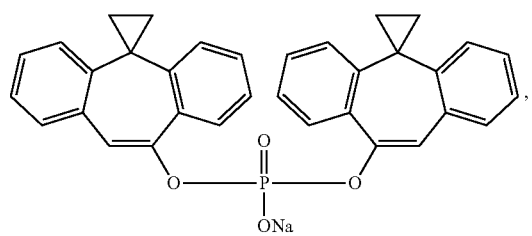
CLH560
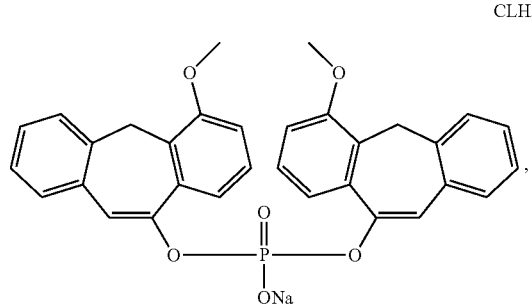
XYF560
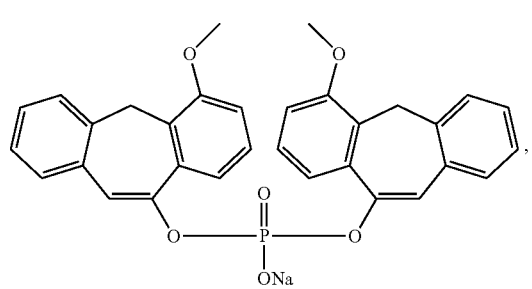
CLH568
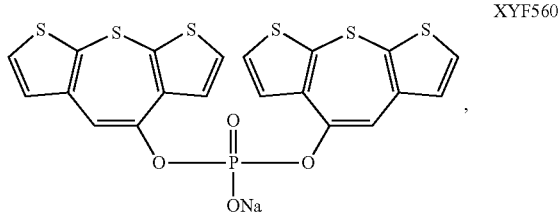
CLH568a
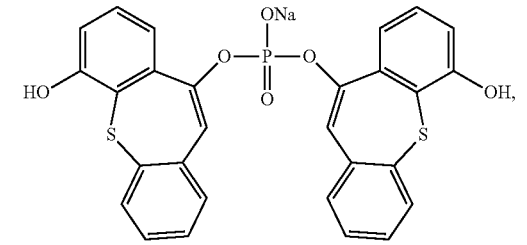
CLH572a
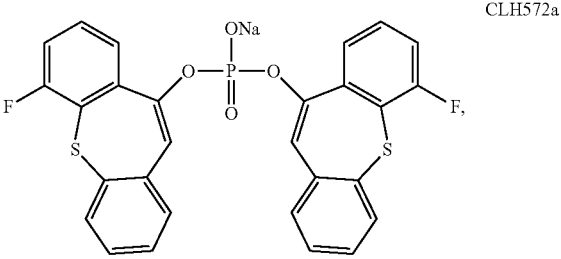
CLH572b
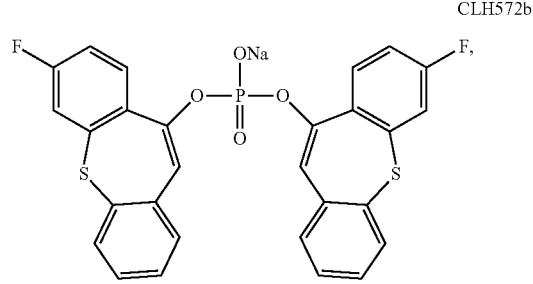
CLH572c
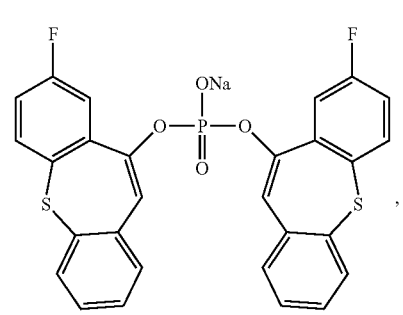
XYF573
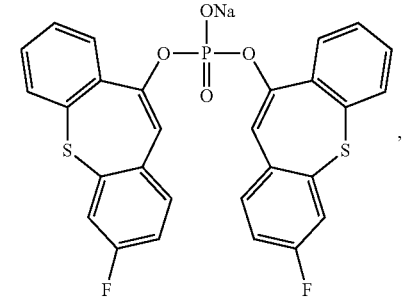
XYF573a
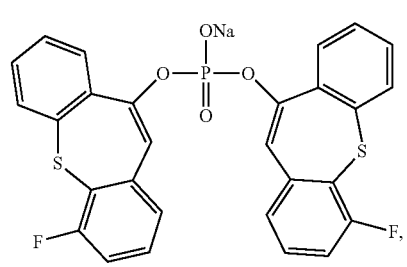
XYF573b
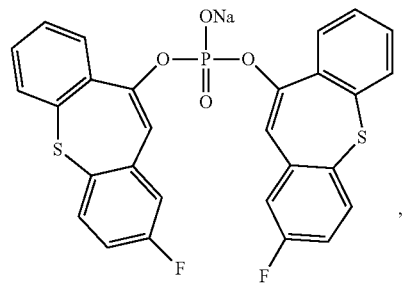

-continued

XYF573c

CLH582

CLH584

CLH596a

CLH596b

-continued

CLH596c

CLH600

XYF608

CLH616a

CLH624

XYF628
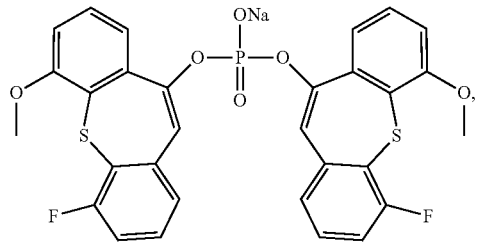
XYF628a
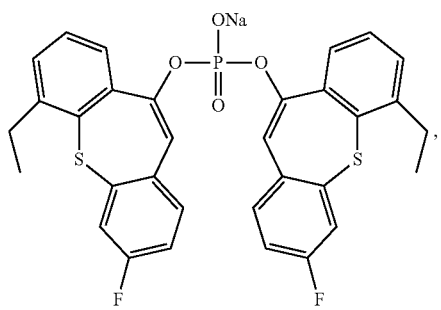
XYF628b
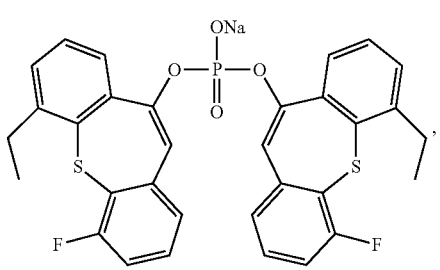
XYF628c
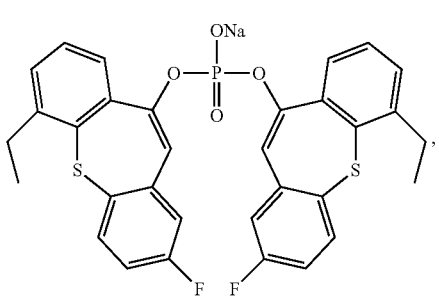
XYF632
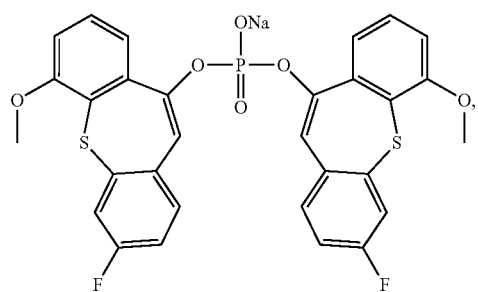
XYF632a
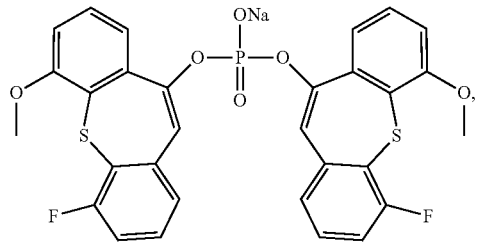
XYF632b
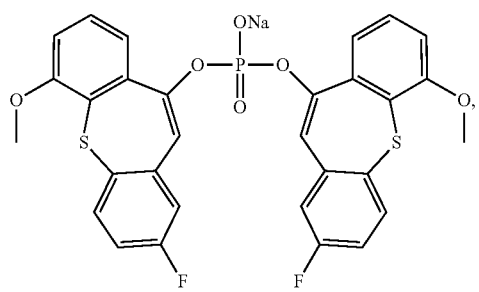
XYF632c
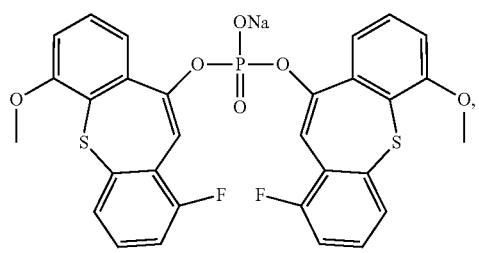
CLH652
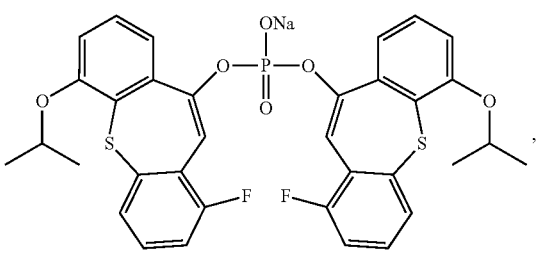
CLH638
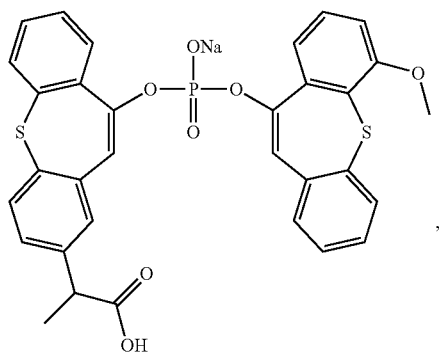

CLH656
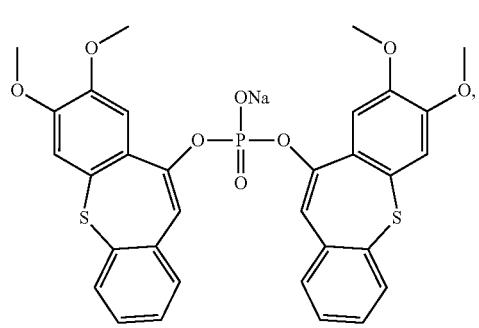
CLH656a
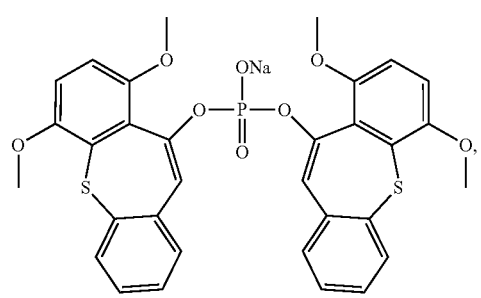
XYF656
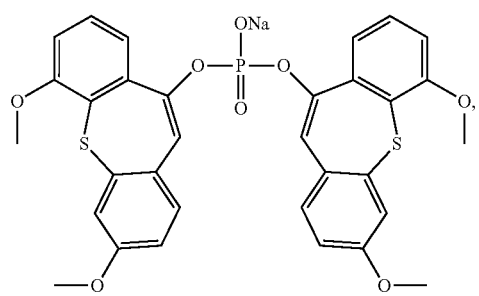
XYF656a
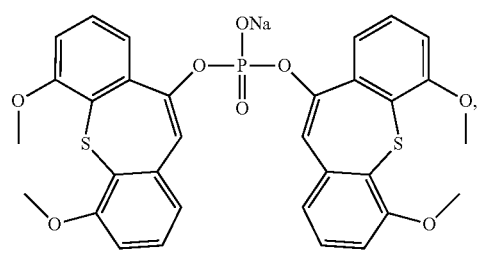
XYF656b
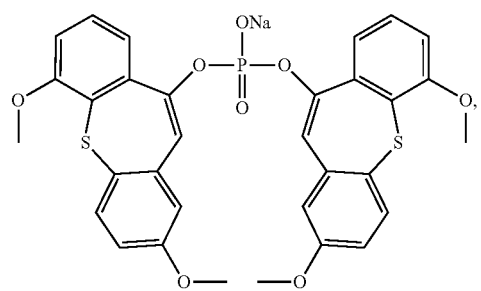
CLH666
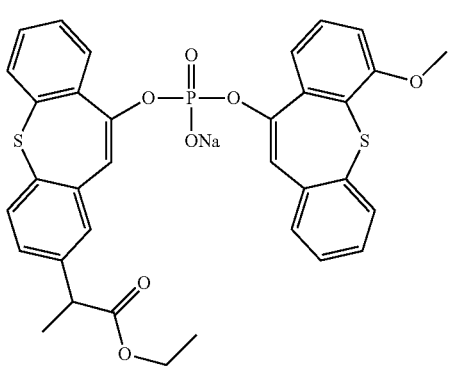
CLH680
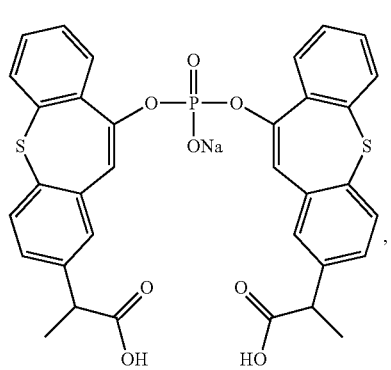
CLH736
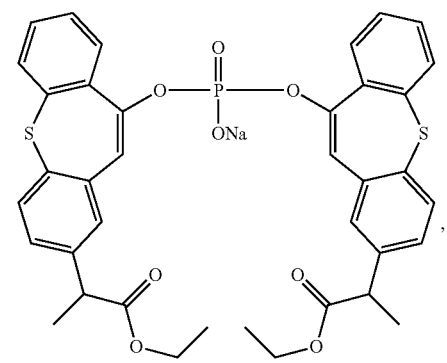
XYF563c
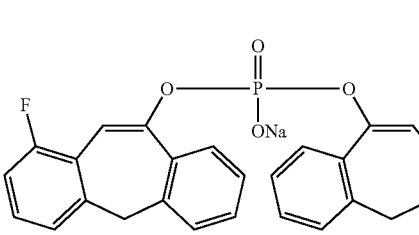
XYF604
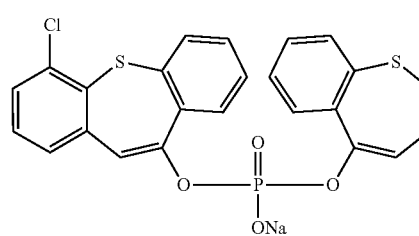

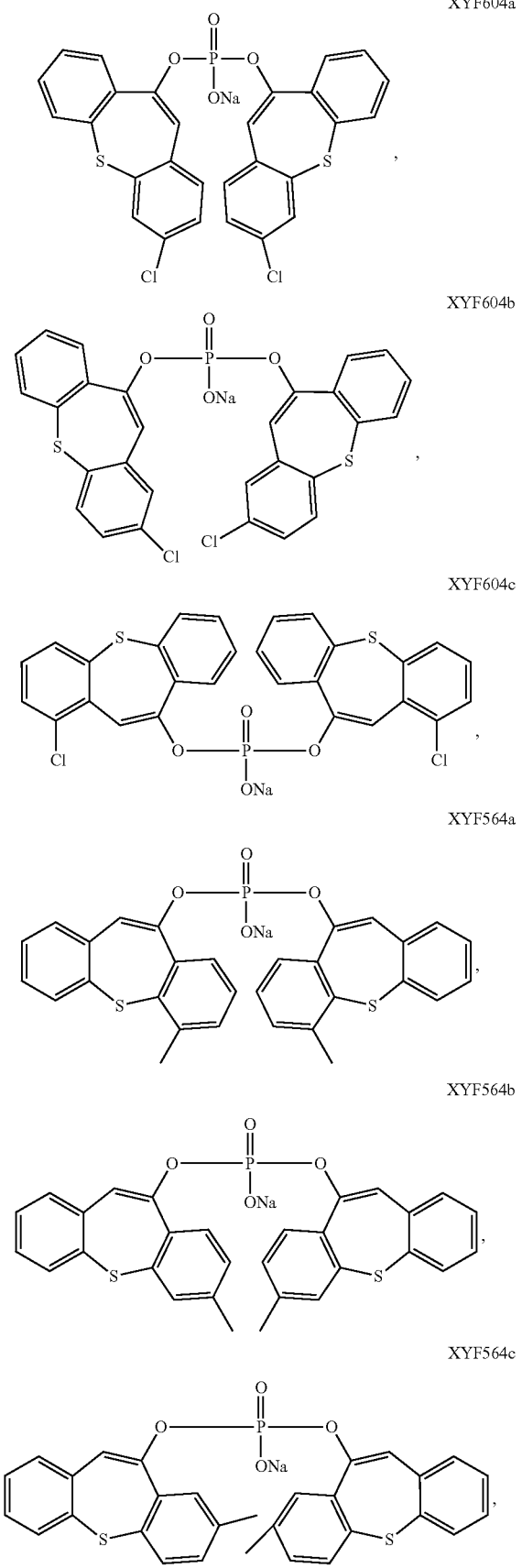

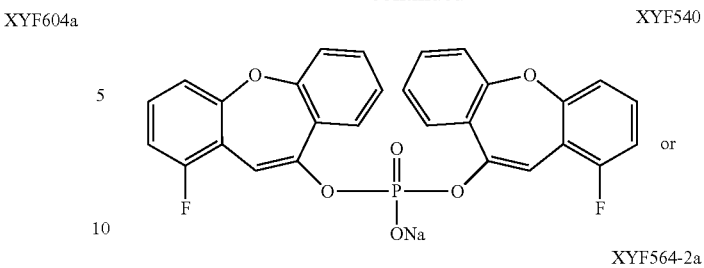

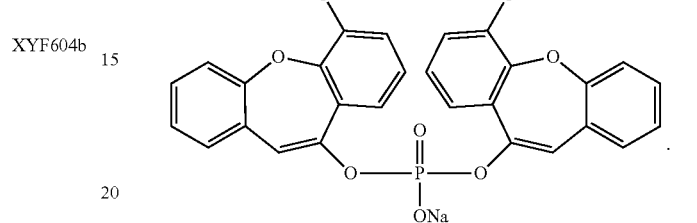

Or in another preferred embodiment, each of the rings and substituents described in formula I is independently a corresponding group of each specific compound described in the specification.

The second aspect of the invention provides a process for the preparation of the compound of the first aspect, the method comprising the step:

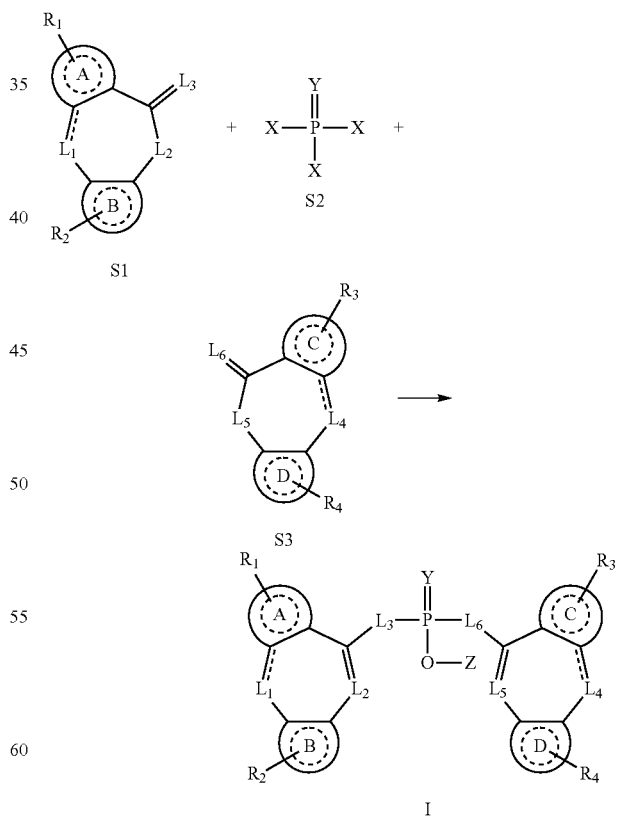

reacting a compound of formula S1, a compound of formula S2 and a compound of formula S3 as starting materials to obtain the compound of formula I, wherein $R_1$, $R_2$, $R_3$, $R_4$, $L_1$, $L_2$, $L_3$, $L_4$, $L_5$, $L_6$, Y, Z, ring A, B, C, and D are as defined above, and ==== represents a single bond or a double bond;

X is F, Cl, Br or I.

The third aspect of the invention provides a process for the preparation of the compound of the first aspect, the method comprising the step:

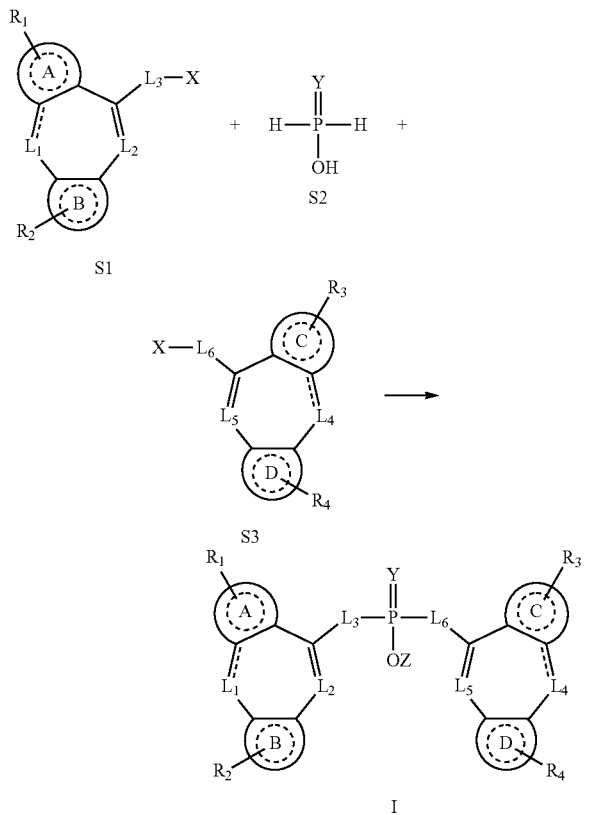

wherein $R_1$, $R_2$, $R_3$, $R_4$, $L_1$, $L_2$, $L_3$, $L_4$, $L_5$, $L_6$, Y, Z, ring A, B, C, and D are as defined above, and ==== represents a single bond or a double bond;

X is F, Cl, Br or I.

The fourth aspect of the invention provides a pharmaceutical composition comprising the compound or the pharmaceutically acceptable salt of the first aspect; and a pharmaceutically acceptable carrier.

The fifth aspect of the invention provides use of the compound or the pharmaceutically acceptable salt of the first aspect or the pharmaceutical composition of the fourth aspect, (i) for the preparation of a GPR84 antagonist;
(ii) as a GPR84 antagonist;
(iii) for the preparation of a medicament for the treatment of a related disease caused by hyper-excitability or high expression of GPR84 receptor.

In another preferred embodiment, the disease is multiple sclerosis, inflammatory bowel disease or arthritis.

The fifth aspect of the present invention provides a method for treating a related disease caused by hyper-excitability or high expression of GPR84 receptor, comprising administering the compound or the pharmaceutically acceptable salt of the present invention to a patient in need thereof.

Unless otherwise defined, all professional and scientific terms used herein have the same meaning known as those skilled in the art. Moreover, any methods and materials similar or equivalent to those described herein may be employed in the methods of the invention. The preferred embodiments and materials described herein are for illustrative purposes only.

It should be understood that within the scope of the present invention, each of the above technical features of the present invention and each of technical features specifically described below (as in the embodiment) can be combined with each other to constitute a new or preferred technical solution. Due to space limitations, they will not be repeated herein.

DETAILED DESCRIPTION OF THE INVENTION

The inventors of the present application have extensively and intensively studied to develop a novel GPR84 antagonist, which can competitively inhibit the activation of the receptor by GPR84 agonist, and can be used for the preparation of a medicament for treating a related disease caused by hyper-excitability or high expression of GPR84 receptor including multiple sclerosis, inflammatory bowel disease, arthritis, and the like. On the basis of this, the present invention has been completed.

Definitions

In the present invention, $C_6$-$C_{10}$ means there are 6 to 10 carbon atoms, and $C_3$-$C_6$ means there are 3 to 6 carbon atoms, and so on.

An integer of 0-4 means 0, 1, 2, 3, 4; and 6-10 carbon atoms means 6, 7, 8, 9, 10 carbon atoms, and so on.

In the present invention, terms such as an aromatic ring, a cycloalkane ring, an alkyl and the like have the same meanings as those familiar to those skilled in the art unless otherwise specified. For example, alkyl refers to a saturated linear or branched hydrocarbyl; for example, —$CH_3$ or —$CH(CH_3)_2$; alkylidene refers to a remaining moiety formed by formally removing two one-valence hydrogens from a saturated hydrocarbyl, including but not limited to methene (—$CH_2$—), ethylene (—$CH_2CH_2$—), and the like. Alkoxy means —O-(alkyl), including but not limited to —$OCH_3$, —$OCH_2CH_3$ and the like. Cycloalkyl refers to a saturated cyclic hydrocarbyl such as a cyclohexyl. Heterocycloalkyl refers to a saturated cyclic hydrocarbyl containing at least one hetero atom (e.g., N, O or S). Heteroaryl refers to an aromatic ring containing at least one hetero atom.

Unless otherwise stated, the aromatic ring, heteroaryl ring, cycloalkane ring, alkyl, alkylidene, alkoxy, cycloalkyl, heterocycloalkyl, and the like described herein include both substituted and unsubstituted moiety, and possible substituent includes, but is not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, hydroxy, halogen, mercapto, cyano, nitro, carboxyl and carboxylate group.

GPR84 Antagonist

The GPR84 antagonist provided by the present invention is a compound having the structure of formula I:

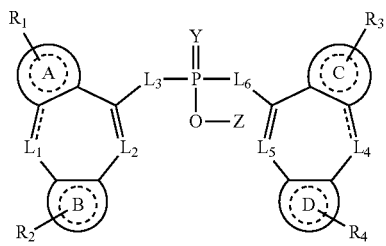
(I)

Each substituent is as defined above.

Most preferably, the compounds of formula I according to the present invention are compounds prepared in the examples.

The invention also provides a pharmaceutically acceptable salt thereof, comprising a salt formed from the reaction of the compound of formula I and an inorganic or organic base compound.

Salts derived from inorganic bases include, but are not limited to, aluminum salts, ammonium salts, calcium salts, copper salts, iron salts, ferrous salts, lithium salts, magnesium salts, manganese salts, manganite salts, potassium salts, sodium salts, zinc salts, etc. Ammonium salts, calcium salts, magnesium salts, potassium salts and sodium salts are particularly preferred.

Salts are derived from pharmaceutically acceptable organic non-toxic bases including, but not limited to, salts of primary, secondary and tertiary amines, substituted amines include naturally occurring substituted amines, cyclic amines and basic ions exchange resin such as arginine, betaine, caffeine, choline, N,N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, glucosamine, aminoglucose, histidine, hydroxocobalamin, isopropylamine, lysine, methyl glucosamine, morpholine, piperazine, piperidine, polyamine resin, procaine, purine, theobromine, triethylamine, trimethylamine, tripropylamine, trometamol, and the like.

Preparation Method

The compound of formula I can be achieved by any of the following routes 1 to 6:

Route 1:

The reaction is carried out in pyridine; the reaction temperature is from 60° C. to 100° C.; the reaction time is about 1 to 24 hours; after the reaction is completed, the reaction mixture is extracted with a solvent such as AcOEt, $Et_2O$, $CH_2Cl_2$, $CHCl_3$ and the like, washed with saturated brine, dried, and subjected to low temperature and reduced pressure to remove the solvent, and the concentrate is subjected to column chromatography to give the desired product confirmed by NMR or the like.

When the starting material S1=S3, two equivalents of the starting material S1 are required for the reaction, and the obtained product P1 has a symmetrical structure. When the starting material S1≠S3, the reaction produces a mixture of three products (P1 to P3), and each product is separated by column chromatography.

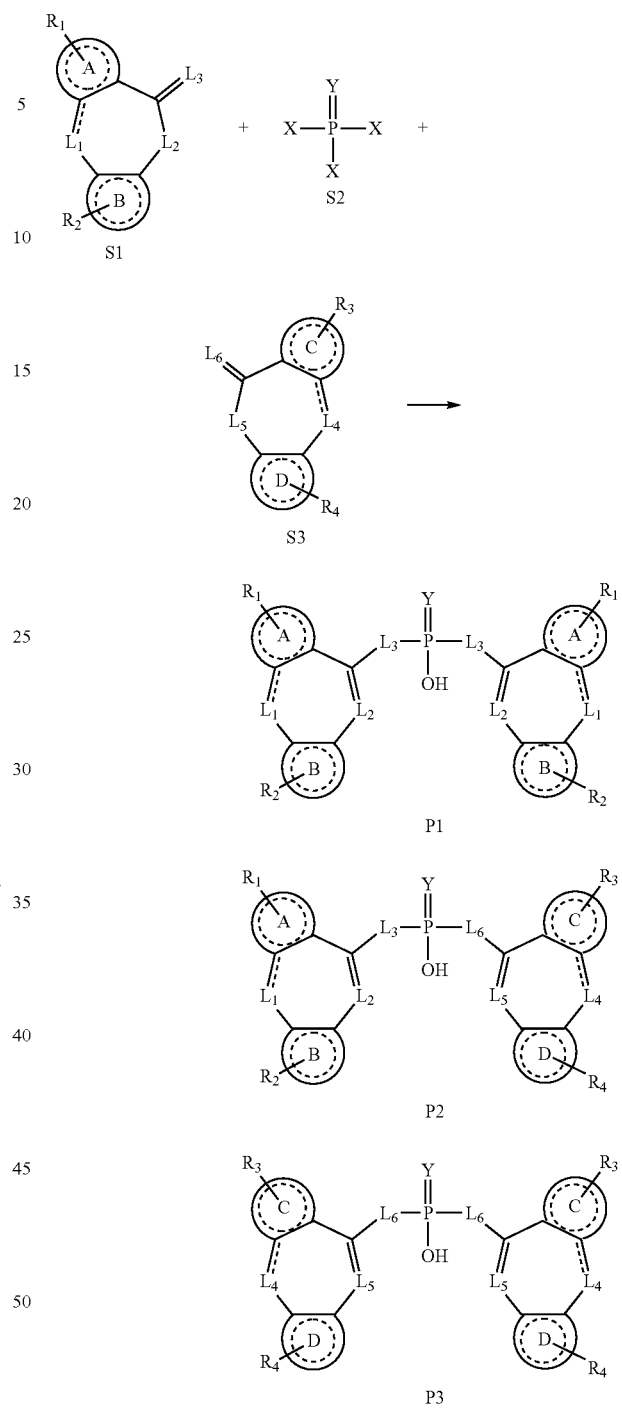

Each substituent is as defined above.

Route 2:

The reaction is carried out in toluene; the base used is hexamethyldisilazane, the reaction temperature is 80° C. to 120° C.; the reaction time is about 1 to 24 hours; after the reaction is completed, the reaction mixture is extracted with a solvent such as AcOEt, $Et_2O$, $CH_2Cl_2$, $CHCl_3$ and the like, washed with a saturated brine, dried, and subjected to low temperature and reduced pressure to remove the solvent, and the concentrate is subjected to column chromatography to give the desired product confirmed by NMR or the like.

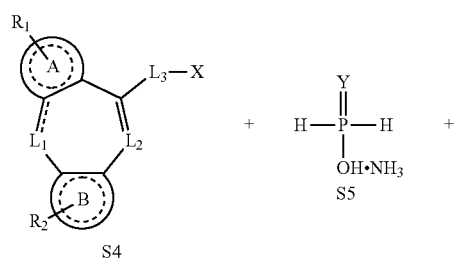

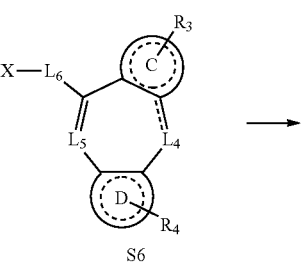

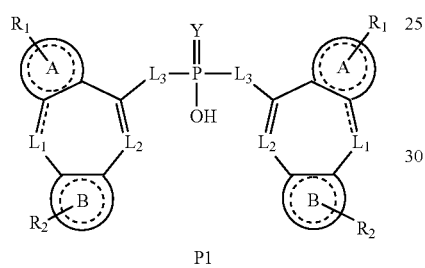

P1

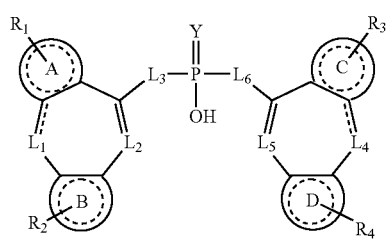

P2

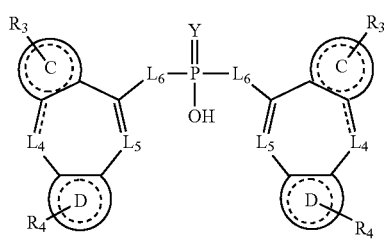

P3

When the starting material S4=S6, two equivalents of the starting material S1 are required for the reaction, and the obtained product P1 has a symmetrical structure. When the starting material S4≠S6, the reaction produces a mixture of three products (P1 to P3), and each product is separated by column chromatography.

Each substituent is as defined above.

Route 3: Salt Formation

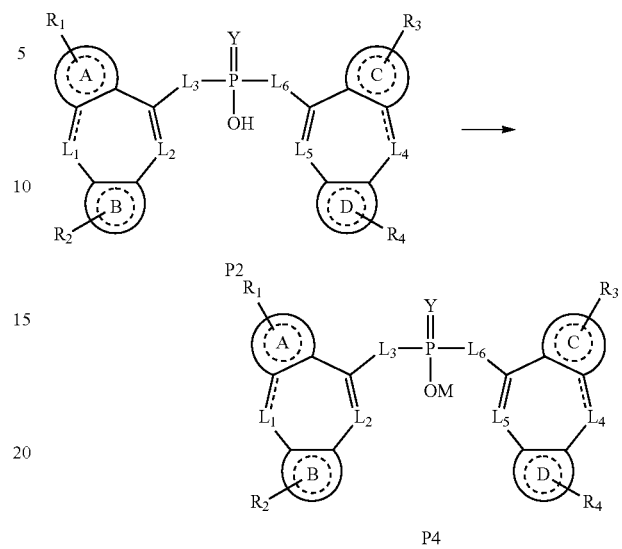

P4

The starting material P2 is dissolved in EA, and washed twice with an aqueous solution, into which a base (the conjugate base of M, the hydroxide of M or the carbonic acid compound of M) is added. The aqueous layer is back-extracted with EA, the EA layer is concentrated, and the crude product is subjected to silica gel column chromatography to obtain the product P4.

M is a cation of the following metals: $L_1$, Na, K, Ca, Mg, Cu, Fe, Zn, Al, Mn;

or a conjugated acid of the following base: NH3, arginine, betaine, caffeine, choline, N,N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, glucosamine, aminoglucose, histidine, hydroxocobalamin, isopropylamine, lysine, methyl glucosamine, morpholine, piperazine, piperidine, polyamine resin, procaine, purine, theobromine, triethylamine, trimethylamine, tripropylamine, trometamol, and the like; and the other substituents are as defined above.

Route 4: Dealkylation

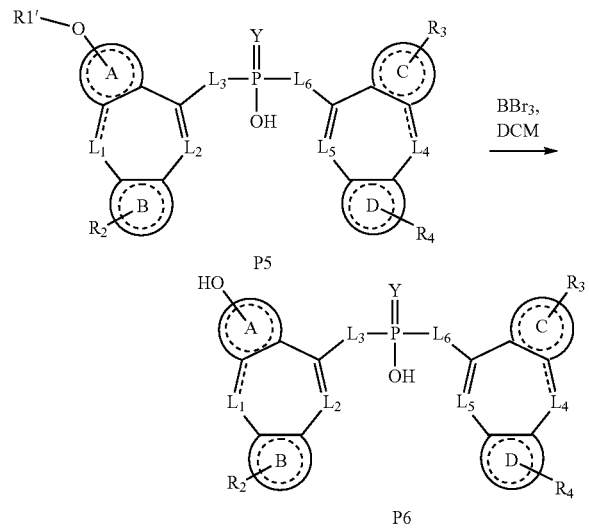

The starting material P5 is dissolved in anhydrous DCM under N$_2$, and a solution of BBr$_3$ in DCM is added dropwise under dry ice-acetone cooling, then gradually warmed to room temperature and stirred overnight. The reaction solution is diluted with water and extracted with EA, EA layer is washed with brine, and the organic phase is concentrated and subjected to silica gel column chromatography to obtain P6.

R1' is a C$_1$-C$_4$ alkyl, and the other substituents are as defined above.

Route 5: Hydrolysis

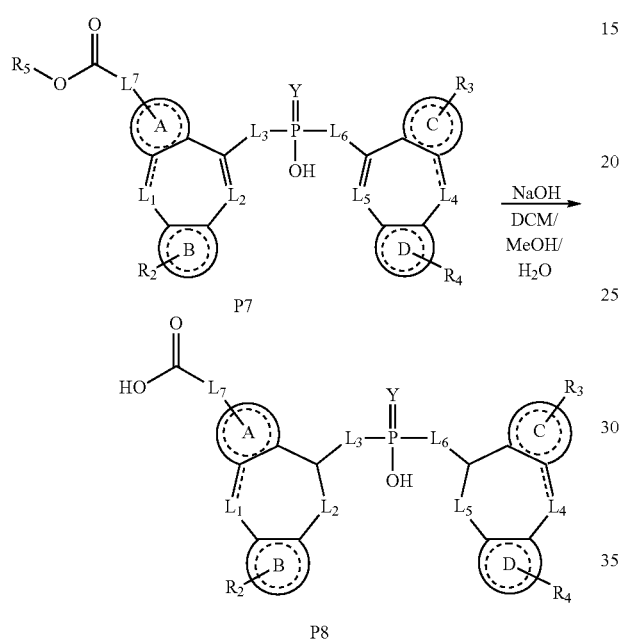

P7

P8

The starting material P7 is dissolved in a mixed solution of DCM/MeOH, and an aqueous NaOH solution is added thereto under stirring at room temperature, and reacted at room temperature. After the reaction is completed, the reaction solution is concentrated under reduced pressure to remove MeOH, and then diluted with water. The pH was adjusted to pH 2 with 1N HCl, then the mixture is extracted with EA, washed with brine, and the organic phase is dried over anhydrous Na$_2$SO$_4$, filtrated, and concentrated to obtain a crude product which is recrystallized from PE/DCM to give the hydrolysate P8.

R$_5$ is a C$_1$-C$_4$ alkyl, and L$_7$ is a C$_1$-C$_4$ alkylidene, and the other substituents are as defined above.

Route 6: Oxidation

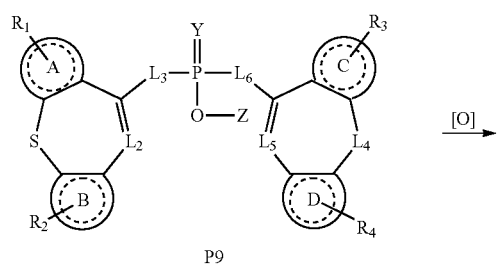

P9

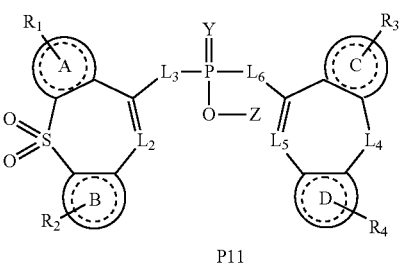

P10

P11

The starting material P9 is dissolved in MeOH, and a solution of Oxone in H$_2$O is added dropwise with stirring at room temperature overnight. The reaction solution is diluted with water, extracted with EA and washed with brine. The organic phase is concentrated and subjected to silica gel column chromatography to obtain P10 and P11.

Use

The compound of the formula I, as an antagonist of GPR84, is capable of competitively inhibiting the activation of the receptor by an agonist of GPR84, and can be used for the preparation of a medicament for treating a disease caused by hyper-excitability or high expression of GPR84 receptor. The diseases include multiple sclerosis, inflammatory bowel disease, arthritis and the like.

Pharmaceutical Composition

The pharmaceutical composition of the present invention comprises a therapeutically effective amount of the compound of formula I or the pharmaceutically acceptable salt thereof, and one or more medicinal carriers.

"Medicinal carrier", "pharmaceutically acceptable carrier" or "pharmacologically available carrier" means one or more compatible solid or liquid filler or gel material which is suitable for human use and which must have sufficient purity and low toxicity. By "compatibility", it is meant herein that each component in the composition is capable of intermixing with the active ingredient of the present invention (the compound of formula I or a pharmaceutically acceptable salt thereof) without significantly reducing the efficacy of the active ingredient. Examples of pharmaceutically acceptable carriers are cellulose and its derivatives (such as sodium carboxymethylcellulose, sodium ethylcellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerin, mannitol, sorbitol, etc.), emulsifier (Tween®), wetting agent (such as sodium dodecyl sulfate), colorant, flavoring agent, stabilizer, antioxidant, preservative, pyrogen-free water and the like.

The compounds and pharmaceutical compositions of the present invention may be in various forms, and may be administered orally in the form of, such as capsule, tablet, granule, solution, powder, pulvis or syrup, or administered in the non-oral form, such as an injection. The compounds and pharmaceutical compositions may be presented in a suitable solid or liquid vehicle and in a suitable sterilizing device for injection or drip. The above formulations can be prepared by conventional pharmaceutical methods.

The compounds and pharmaceutical compositions of the present invention are useful for clinical use in mammals, including humans and animals, and can be administered by the oral, nasal or gastrointestinal routes. The most preferred route of administration is oral.

The above features mentioned in the present invention, or the features mentioned in the embodiments, may be arbitrarily combined. All of the features disclosed in the present specification can be used in combination with any of the compositions, and each of the various features disclosed in the specification can be replaced by any alternative feature that provides the same, equal or similar purpose. Therefore, unless otherwise stated, the disclosed features are only general examples of equal or similar features.

The invention is further illustrated below in conjunction with specific examples. It is to be understood that the examples are for illustrative purposes only and are not intended to limit the scope of the invention. The experimental methods in the following examples which do not specify the specific conditions are usually carried out according to the conventional conditions, such as the conditions described in Sambrook et al., Molecular Cloning: Laboratory Manual (New York: Cold Spring Harbor Laboratory Press, 1989), or according to the conditions suggested by the manufacturer. Unless otherwise stated, percentages and parts are by weight.

In the following examples, NMR was measured using a Mercury-VX 300M or Mercury-VX400M instrument manufactured by Varian (NMR calibration: δ H 7.26 ppm (CDCl$_3$), 2.50 ppm (DMSO-d$_6$), 3.15 ppm (CD$_3$OD)). The reagents were mainly provided by Shanghai Chemical Reagent Co., Ltd. TLC thin layer chromatography silica gel plate (model, HSGF 254) is produced by Shandong Yantai Huiyou Silicone Development Co., Ltd. The normal phase column chromatography silica gel used for compound purification (model zcx-11, 200-300 mesh) is produced by Branch Factory of Shandong Qingdao Marine Chemical Plant.

Example 1

Preparation of Compound CLH514

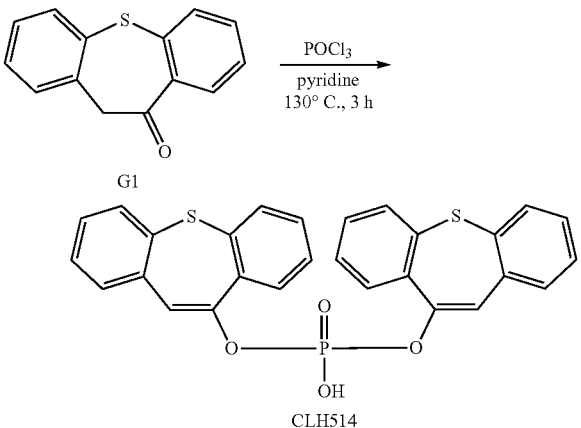

G1 was synthesized by referring to *J. Med. Chem.* 2010, 53, 7021-7034; and PCT Int. Appl., 2009016085, 5 Feb. 2009. Some analogs of G1 can be purchased from reagent companies, and the others were prepared using the same or similar routes as for the synthesis of G1.

The starting material G1 (510 mg, 2.25 mmol) was dissolved in dry pyridine (2.5 mL), and then double-distilled POCl$_3$ (207 μL, 2.25 mmol) was added dropwise under N$_2$ and reacted at 130° C. for 3 h. The reaction solution was cooled to room temperature, diluted with water, adjusted to pH2 with 6 N HCl and then extracted with EA. The aqueous layer was back-extracted three times, dried over anhydrous Na$_2$SO$_4$, filtrated, concentrated, and then subjected to silica gel column chromatography (DCM/MeOH=20/1-10/1) to obtain the desired compound CLH514 (230 mg, 40%, white solid). $^1$H NMR (d$_6$-DMSO, 300 MHz): δ 7.63 (d, J=7.2 Hz, 2H), 7.41-7.50 (m, 4H), 7.20-7.40 (m, 12H), 3.56 (br, 1H).

The following compounds were synthesized in the same manner:

| No. | Structure formula | $^1$H NMR data |
|---|---|---|
| CLH478 | | $^1$H NMR (CDCl$_3$, 300 MHz): δ 7.64 (d, J = 7.5 Hz, 2H), 7.25 (s, 2H), 6.78-7.10 (m, 14H), 3.36 (s, 4H), 3.00 (br, 1H). |
| CLH482 | | $^1$H NMR (CDCl$_3$, 300 MHz): δ 7.43 (d, J = 7.5 Hz, 2H), 6.90-7.10 (m, 12H), 6.69 (t, J = 6.9 Hz, 4H), 3.59 (br, 1H). |

| No. | Structure formula | ¹H NMR data |
|---|---|---|
| CLH508 | 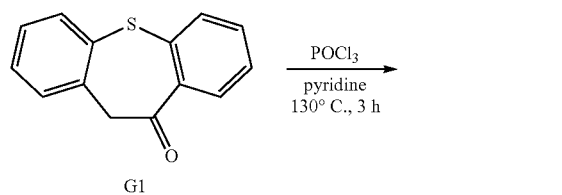 | ¹H NMR (d₆-DMSO, 300 MHz): δ 7.35-7.55 (m, 2H), 7.10-7.35 (m, 4H), 6.80-7.10 (m, 12H), 3.34 (s, 1H), 3.17 (s, 3H), 3.12 (s, 3H). |

Example 2

Preparation of Compound CLH536

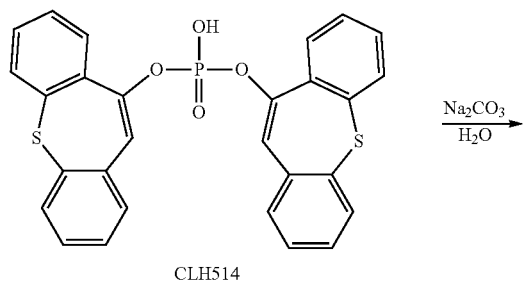

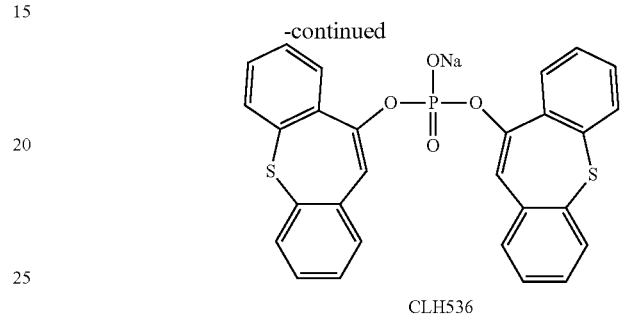

The starting material G1 (2.635 g, 11.64 mmol) was dissolved in dry pyridine (10 mL), and then double-distilled POCl₃ (0.610 mL, 6.64 mmol) was added dropwise under N₂ and reacted at 130° C. for 3 h. The reaction solution was cooled to room temperature, diluted with water, adjusted to pH2 with 6 N HCl and then extracted with EA. The EA layer was washed with saturated Na₂CO₃ solution. The aqueous layer was back-extracted three times, dried over anhydrous Na₂SO₄, filtrated, concentrated, and then subjected to silica gel column chromatography (DCM/MeOH=10/1) to obtain the desired compound CLH536 (2.247 g, 72%, white solid).
¹H NMR (d₆-DMSO, 300 MHz): δ 7.72 (dd, J=5.4 Hz, 1.8 Hz, 2H), 7.40-7.44 (m, 4H), 7.15-7.35 (m, 12H).

The following compounds were synthesized in the same manner.

| No. | Structure formula | ¹H NMR data |
|---|---|---|
| CLH472 |  | ¹H NMR (d₆-DMSO, 300 MHz): δ 8.76 (d, J = 8.4 Hz, 2H), 8.65-8.72 (m, 2H), 8.27 (d, J = 8.1 Hz, 2H), 7.85 (s, 2H), 7.70-7.75 (m, 2H), 7.65 (t, J = 6.9 Hz, 2H), 7.45-7.60 (m, 6H). |
| CLH472a |  | ¹H NMR (d₆-DMSO, 300 MHz): δ 8.73 (d, J = 8.4 Hz, 4H), 8.33 (s, 2H), 8.06 (d, J = 8.4 Hz, 4H), 7.48 (t, J = 7.2 Hz, 4H), 7.39 (t, J = 7.2 Hz, 4H) |

| No. | Structure formula | ¹H NMR data |
|---|---|---|
| CLH524 | | ¹H NMR (CDCl₃, 300 MHz): δ 7.35 (d, J = 8.1 Hz, 1H), 7.20-7.28 (m, 1H), 6.72-7.10 (m, 16H), 6.50-6.70 (m, 4H). |
| CLH524a | | ¹H NMR (CDCl₃, 300 MHz): δ 7.60-7.70 (m, 2H), 7.00-7.20 (m, 10H), 6.80-7.00 (m, 6H), 4.80-5.00 (m 4H). |
| CLH528 | | ¹H NMR (CDCl₃, 300 MHz): δ 8.13-8.16 (m, 2H), 8.01-8.04 (m, 2H), 7.60-7.75 (m, 6H), 7.40-7.50 (m, 2H), 7.28-7.40 (m, 4H), 6.80 s, 2H). |
| CLH528a | | ¹H NMR (CDCl₃, 400 MHz): δ 7.35-7.40 (m, 4H), 7.15-7.25 (m, 8H), 7.10-7.16 (m, 4H), 6.40-6.60 (br, 2H), 4.20 (q, J = 6.6 Hz, 2H), 1.62 (s, 6H). |
| XYF528 | | ¹H NMR (CDCl₃, 400 MHz): δ 7.27 (s, 2H), 6.86-6.97 (m, 14H), 6.75 (s, 2H), 3.04-3.14 (m, 8H). |
| CLH544 | | ¹H NMR (CDCl₃, 300 MHz): δ 7.47-7.72 (br, 2H), 7.01-7.25 (br, 2H), 6.71-7.69 (br, 2H), 6.36-6.62 (br, 2H), 3.70 (s, 6H), 3.00-3.20 (br, 4H), 2.26-2.56 (br, 4H), 1.20-1.60 (m, 8H). |

| No. | Structure formula | $^1$H NMR data |
|---|---|---|
| CLH544a | | $^1$H NMR (CDCl$_3$, 300 MHz): δ 7.55-7.47 (m, 4H), 7.30-7.15 (m, 4H), 6.72 (s, 2H), 2.41 (t, J = 12.5 Hz, 4H), 2.32 (t, J = 12.0 Hz, 4H), 1.80-1.67 (m, 4H), 1.65-1.52 (m, 4H). |
| CLH548 | | $^1$H NMR (CDCl$_3$, 300 MHz): δ 7.28-7.35 (m, 2H), 7.08-7.18 (m, 8H), 7.02-7.08 (m, 2H), 6.77 (s, 2H). |
| CLH552 | | $^1$H NMR (CDCl$_3$, 300 MHz): δ 7.72 (d, J = 6.6 Hz, 1H), 7.60 (d, J = 6.6 Hz, 1H), 7.34 (s, 2H), 7.16 (s, 4H), 6.88-7.10 (m, 6H), 6.60-6.88 (m, 4H), 1.16-1.36 (br, 3H), 1.11 (t, J = 6.3 Hz, 1H), 0.35-0.60 (m, 2H), 0.15-0.35 (br, 2H). |
| CLH560 | | $^1$H NMR (CDCl$_3$, 300 MHz): δ 7.20-7.30 (m, 4H), 7.13 (d, J = 7.8 Hz, 2H), 6.90-7.06 (m, 4H), 6.66-6.86 (m, 4H), 6.57 (d, J = 8.1 Hz, 2H), 3.66 (s, 6H), 3.40-3.58 (br, 4H). |
| XYF560 | | $^1$H NMR (CDCl$_3$, 300 MHz): δ 7.85-8.1 (m, 4H), 6.50-7.10 (m, 6H). |
| CLH572a | | $^1$H NMR (CDCl$_3$, 300 MHz): δ 7.30-8.00 (br, 5H), 6.10-7.20 (m, 11H). |

| No. | Structure formula | ¹H NMR data |
|---|---|---|
| CLH572b | | ¹H NMR (CDCl₃, 300 MHz): δ 7.15-8.00 (br, 6H), 6.60-7.13 (m, 7H), 6.00-6.60 (br, 3H). |
| CLH572c | | ¹H NMR (CDCl₃, 300 MHz): δ 7.30-8.50 (m, 6H), 6.10-7.20 (m, 10H). |
| XYF573 | | ¹H NMR (d₆-DMSO, 300 MHz): δ 7.71 (d, J = 7.2 Hz, 2H), 7.15-7.42 (m, 14H). |
| XYF573a | | ¹H NMR (d₆-DMSO, 300 MHz): δ 7.71 (d, J = 9.0 Hz, 2H), 7.17-7.48 (m, 12H), 7.02 (d, J = 7.8 Hz, 2H). |
| XYF573b | | ¹H NMR (d₆-DMSO, 300 MHz): δ 7.71 (d, J = 6.9 Hz, 2H), 7.32-7.48 (m, 10H), 7.06-7.10 (m, 2H), 6.97 (d, J = 10.2 Hz, 2H). |

-continued

| No. | Structure formula | ¹H NMR data |
|---|---|---|
| XYF573c | | ¹H NMR (d₆-DMSO, 300 MHz): δ 7.73 (d, J = 7.8 Hz, 2H), 7.15-7.46 (m, 14H). |
| CLH596a | | ¹H NMR (CDCl₃, 300 MHz): δ 7.40 (d, J = 8.4 Hz, 2H), 7.30 (s, 2H), 7.22 (d, J = 7.8 Hz, 2H), 7.03 (t, J = 7.2 Hz, 4H), 6.88-7.00 (m, 4H), 6.59 (d, J = 7.2 Hz, 2H), 3.67 (s, 6H). |
| CLH596b | | ¹H NMR (CDCl₃, 300 MHz): δ 7.30-7.70 (br, 4H), 7.10-7.30 (br, 2H), 6.50-7.10 (m, 8H), 6.00-6.50 (br, 2H), 3.49 (s, 6H). |
| CLH596c | | ¹H NMR (CDCl₃, 300 MHz): δ 7.32-7.60 (br, 2H), 7.17-7.30 (br, 2H), 6.85-7.17 (m, 8H), 6.70-6.85 (br, 2H), 6.45-6.65 (br, 2H), 3.34 (s, 6H). |
| XYF608 | | ¹H NMR (CDCl₃, 300 MHz): δ 7.15-7.23 (m, 4H), 6.86-6.96 (m, 4H), 6.58-6.63 (m, 4H), 3.67 (s, 6H) |

| No. | Structure formula | ¹H NMR data |
|---|---|---|
| CLH616a | | ¹H NMR (CDCl₃, 300 MHz): δ 7.46-7.52 (m, 4H), 7.28-7.44 (m, 8H), 7.12-7.22 (m, 4H), 6.75 (s, 2H), 4.15-4.35 (m, 8H). |
| CLH624 | | ¹H NMR (CDCl₃, 300 MHz): δ 7.30-7.52 (m, 4H), 7.12-7.23 (m, 2H), 6.94-7.12 (m, 4H), 6.73-6.93 (m, 4H), 6.50-6.68 (m, 2H), 3.90 (q, J = 6.6 Hz, 4H), 1.37 (t, J = 6.6 Hz, 6H). |
| XYF628 | | ¹H NMR (d₆-DMSO, 300 MHz): δ 7.55 (d, J = 7.5 Hz, 2H), 7.31-7.36 (m, 6H), 7.16-7.23 (m, 6H), 2.94 (q, J = 7.5 Hz, 4H), 1.17 (t, J = 7.5 Hz, 3H). |
| XYF628a | | ¹H NMR (d₆-DMSO, 300 MHz): δ 7.55 (d, J = 7.5 Hz, 2H), 7.16-7.40 (m, 10H), 7.03 (d, J = 9.6 Hz, 2H), 2.97 (q, J = 7.5 Hz, 4H), 1.18 (t, J =7.5 Hz, 3H). |
| XYF628b | | ¹H NMR (d₆-DMSO, 300 MHz): δ 7.54-7.56 (m, 4H), 7.31-7.34 (m, 4H), 7.20 (t, J = 7.5 Hz, 2H), 7.09 (t, J = 8.4 Hz, 2H), 6.95 (d, J = 9.6 Hz, 2H), 2.93 (q, J = 7.5 Hz, 4H), 1.16 (t, J = 7.5 Hz, 3H). |

-continued

| No. | Structure formula | ¹H NMR data |
|---|---|---|
| XYF628c | | ¹H NMR (d₆-DMSO, 300 MHz): δ 7.56 (d, J = 7.2 Hz, 2H), 7.15-7.43 (m, 12H), 2.93 (q, J = 7.5 Hz, 4H), 1.17 (t, J = 7.5 Hz, 3H). |
| XYF632 | | ¹H NMR (CDCl₃, 400 MHz): δ 7.21 (s, 2H), 7.08-7.13 (m, 4H), 6.84-6.91 (m, 4H), 6.61 (d, J = 8.0 Hz, 2H), 6.50-6.58 (m, 2H), 3.69 (s, 6H). |
| XYF632a | | ¹H NMR (d₆-DMSO, 400 MHz): δ 7.35 (s, 2H), 7.27-7.30 (m, 6H), 7.14 (t, J = 8.8 Hz, 2H), 7.07 (dd, J = 2.0 Hz, 7.6 Hz, 2H), 6.98 (d, J = 8.0 Hz, 2H), 3.82 (s, 6H). |
| XYF632b | | ¹H NMR (d₆-DMSO, 400 MHz): δ 7.14-7.29 (m, 12H), 7.05 (d, J = 8.0 Hz, 2H), 3.81 (s, 6H). |
| XYF632c | | ¹H NMR (d₆-DMSO, 400 MHz): δ 7.39 (s, 2H), 7.17-7.32 (m, 10H), 7.06 (d, J = 8.0 Hz, 2H), 3.81 (s, 6H). |

-continued
| No. | Structure formula | ¹H NMR data |
|---|---|---|
| CLH652 | 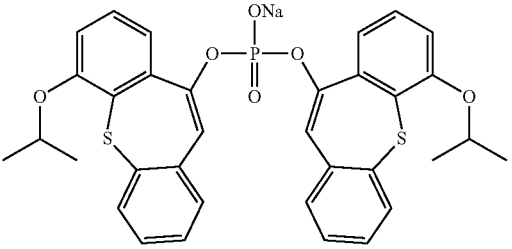 | ¹H NMR (CDCl₃, 300 MHz): δ 7.29-7.46 (d, J = 6.9 Hz, 4H), 7.15-7.25 (m, 2H), 6.96-7.10 (m, 4H), 6.75-6.96 (m, 4H), 6.58-6.73 (d, J = 6.6 Hz, 2H), 4.15-4.39 (m, 2H), 1.26 (d, J = 6.0 Hz, 12H). |
| CLH656 | 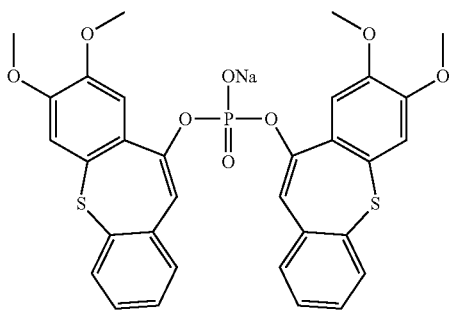 | ¹H NMR (CDCl₃, 300 MHz): δ 7.40 (s, 2H), 7.20-7.34 (m 2H), 6.80-7.10 (m, 8H), 6.72 (s, 2H), 3.75 (s, 6H), 3.28 (s, 6H). |
| CLH656a | 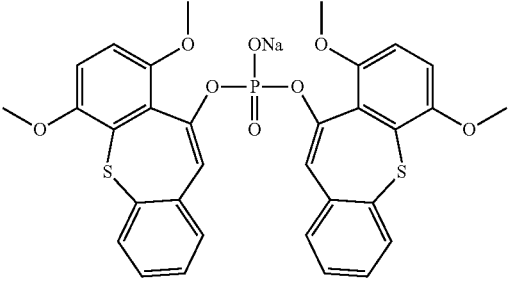 | ¹H NMR (CDCl₃, 300 MHz): δ 7.43-7.46 (m, 2H), 7.06-7.23 (m, 8H), 6.59-6.74 (m, 4H), 3.74 (s, 3H), 3.73 (s, 3H), 3.60 (s, 6H). |
| XYF656 | 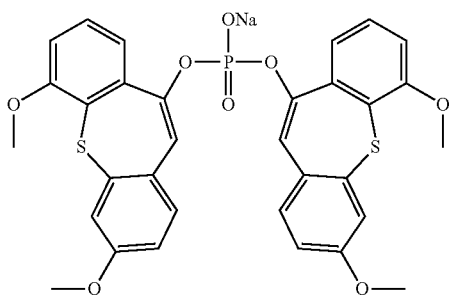 | ¹H NMR (CDCl₃, 400 MHz): δ 7.25-7.28 (m, 4H), 6.92-6.95 (m, 6H), 6.59 (d, J = 4.0 Hz, 2H), 6.45 (d, J = 4.0 Hz, 2H), 3.70 (s, 6H), 3.63 (s, 6H). |
| XYF656a | 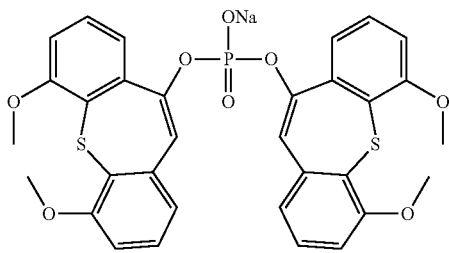 | ¹H NMR (d₆-DMSO, 400 MHz): δ 7.30 (s, 2H), 7.28 (d, J = 1.6 Hz, 2H), 7.17-7.22 (m, 4H), 7.02 (d, J = 8.0 Hz, 2H), 6.91 (d, J = 8.0 Hz, 2H), 6.73 (d, J = 8.0 Hz, 2H), 3.80 (s, 12H). |

-continued

| No. | Structure formula | ¹H NMR data |
| --- | --- | --- |
| XYF656b | | ¹H NMR (d₆-DMSO, 400 MHz): δ 7.30-7.34 (m, 6H), 7.21 (t, J = 8.0 Hz, 2H), 7.03 (d, J = 8.0 Hz, 2H), 6.77 (dd, J = 4.0 Hz, 12.0 Hz, 2H), 6.66 (d, J = 4.0 Hz, 2H), 3.81 (s, 12H), (3.68, 2H). |
| CLH736 | | ¹H NMR (CDCl₃, 300 MHz): δ 7.57 (d, J = 7.5 Hz, 2H), 7.20-7.40 (m, 6H), 6.90-7.15 m, 8H), 3.93 (q, J = 7.2 Hz, 4H), 3.44 (q, J = 7.2 Hz, 2H), 1.24 (d, J = 7.2 Hz, 6H), 1.04 (t, J = 7.2 Hz, 6H). |
| XYF536c | | 1H NMR (d6-DMSO, 300 MHz): δ 7.65 (d, J = 7.5 Hz, 2H), 7.14-7.34 (m, 12H) 6.98-7.04 (m, 2H), 3.59 (s, 4H) |
| XYF604 | | 1H NMR (d6-DMSO, 500 MHz): δ 7.71 (d, J = 7.5 Hz, 2H), 7.45-7.49 (m, 4H), 7.34-7.41 (m, 6H), 7.26 (t, J = 7.5 Hz, 2H), 7.15 (d, J = 8.0 Hz, 2H) |
| XYF604a | | 1H NMR (d6-DMSO, 500 MHz): δ 7.70 (d, J = 8.0 Hz, 2H), 7.51 (dd, J = 7.5 Hz, 1.0 Hz, 2H), 7.30-7.39 (m, 8H), 7.20 (d, J = 8.5 Hz, 2H) |
| XYF604b | | 1H NMR (d6-DMSO, 300 MHz): δ 7.71 (d, J = 7.8 Hz, 2H), 7.28-7.45 (m, 12H), 7.17 (d, J = 2.1, 2H). |

| No. | Structure formula | $^1$H NMR data |
|---|---|---|
| XYF604c | | 1H NMR (d6-DMSO, 300 MHz): δ 7.69 (d, J = 7.2 Hz, 2H), 7.54 (s, 2H) 7.22-7.47 (m, 12H) |
| XYF564a | | 1H NMR (d6-DMSO, 500 MHz): δ 7.58 (d, J = 7.5 Hz, 2H), 7.52 (d, J = 7.5 Hz, 2H), 7.38 (s, 2H), 7.32-7.21 (m, 8H), 7.16 (t, J = 7.5 Hz, 2H), 2.53 (s, 6H) |
| XYF564b | | 1H NMR (d6-DMSO, 500 MHz): δ 7.63 (d, J = 8.0 Hz, 2H), 7.44 (dd, J = 7.5, 1.0 Hz, 2H), 7.34 (s, 2H), 7.30-7.22 (m, 6H), 7.18 (d, J = 7.5 Hz, 2H), 7.11 (d, J = 7.5 Hz, 2H), 2.26 (s, 6H) |
| XYF564c | | 1H NMR (d6-DMSO, 500 MHz): δ 7.49 (s, 2H), 7.44 (d, J = 8.0 Hz, 2H), 7.38 (s, 2H), 7.32-7.21 (m, 6H), 7.20 (d, J = 7.5 Hz, 2H), 7.15 (dd, J = 8.0, 1.5 Hz, 2H), 2.14 (s, 6H) |
| XYF540 | | 1H NMR (d6-DMSO, 500 MHz): 7.62 (dd, J = 8.0, 2.0 Hz, 2H), 7.41 (td, J = 8.0, 2.0 Hz, 2H), 7.31-7.24 (m, 4H), 7.16 (td, J = 8.0, 1.5 Hz, 2H), 7.12-7.03 (m, 6H) |
| XYF564-2a | | 1H NMR (d6-DMSO, 500 MHz): δ 7.26-7.23 (m, 2H), 7.20-7.05 (m, 10H), 6.96 (s, 12H), 3.86 (s, 6H) |

Example 3

Preparation of Compound CLH666

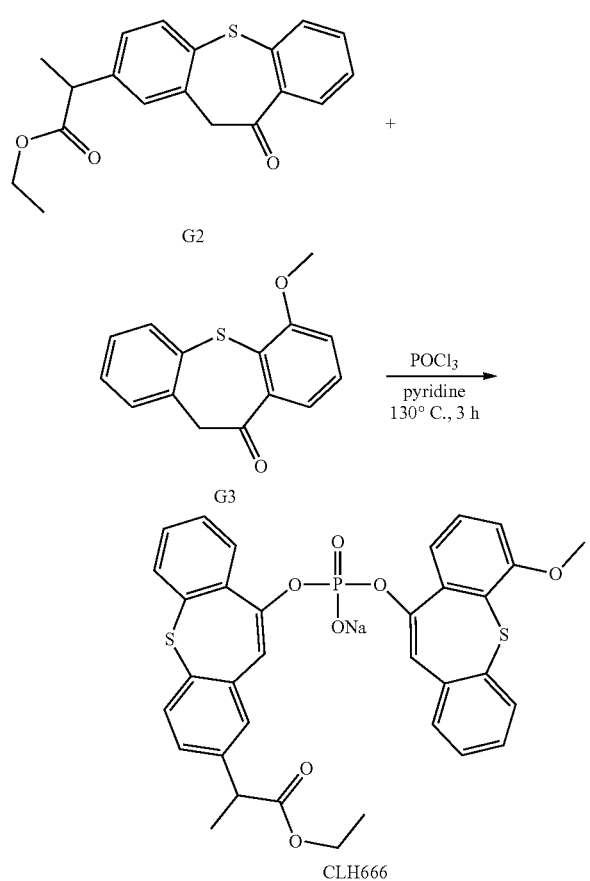

The starting material G2 was purchased from a reagent company, and the synthesis of the starting material G3 was carried out in the same synthetic route as G1.

The starting materials G2 (62.7 mg, 0.192 mmol) and G3 (49.2 mg, 0.192 mmol) were dissolved in dry pyridine (0.5 mL), and then double-distilled $POCl_3$ (21 μL, 0.230 mmol) was added dropwise under $N_2$ and reacted at 130° C. for 3 h. The reaction solution was diluted with EA, then diluted with water, adjusted to pH1 with 6 N HCl and then extracted with EA three times. The EA layer was washed with saturated brine and then saturated $Na_2CO_3$ solution. The organic phase was concentrated and subjected to silica gel column chromatography (DCM/MeOH=20/1-6/1) to obtain the desired compound CLH666 (23 mg, 18%, white solid). $^1$H NMR ($CDCl_3$, 300 MHz): δ 7.53 (d, J=6.9 Hz, 1H), 7.42 (d, J=7.8 Hz, 1H), 7.16-7.37 (m, 5H), 6.83-7.16 (m, 8H), 6.61 (d, J=8.4 Hz, 1H), 3.75-4.00 (m, 2H), 3.69 (s, 3H), 3.43 (q, J=6.9 Hz, 1H), 1.22 (d, J=6.9 Hz, 3H), 1.01 (t, J=6.9 Hz, 3H).

Example 4

Preparation of Compounds CLH568 and CLH582

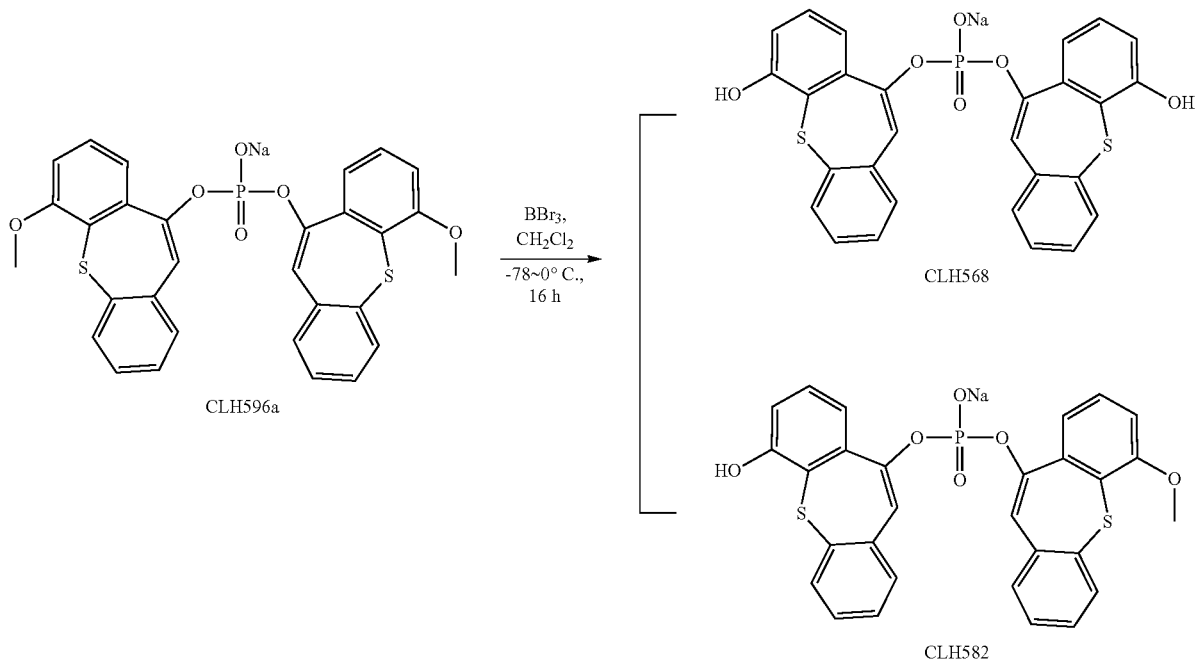

The starting material, CLH596a (45.2 mg, 0.076 mmol), was dissolved in dry EtOAc (1 mL). 2N solution of BBr3 in DCM ((190 μL, 0.3 mmol) was added dropwise under $N_2$ and dry ice-acetone cooling, then gradually warmed to room temperature and stirred overnight. The reaction solution was diluted with water and extracted with EA three times. The EA layer was washed with brine and then saturated $Na_2CO_3$ solution. The organic phase was concentrated and purified by silica gel preparation plate (DCM/MeOH=20/1-6/1, developed twice) to obtain the desired compounds.

CLH568 (18.3 mg, 42.3%, white solid). $^1$H NMR (d$_6$-DMSO, 300 MHz): δ 9.50-9.70 (br, 2H), 7.47 (d, J=6.3 Hz, 2H), 7.10-7.35 (m, 10H), 7.04 (t, J=7.8 Hz, 2H), 6.89 (J=7.8 Hz, 2H).

CLH582 (11.2 mg, 25.3%, white solid). $^1$H NMR (CDCl$_3$, 300 MHz): δ 7.30-7.40 (m, 3H), 7.15-7.26 (m, 3H), 7.12 (d, J=7.2 Hz, 1H), 6.70-7.05 (m, 8H), 6.38 (d, J=8.1 Hz, 1H), 3.61 (s, 3H).

Example 5

Preparation of Compound CLH680

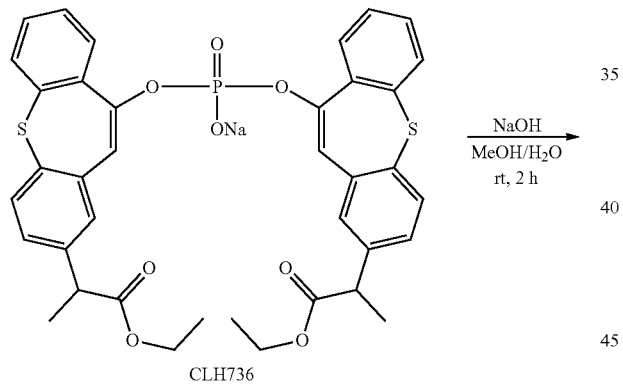

The starting material CLH736 (13 mg, 0.018 mmol) was dissolved in 4 mL of methanol, and 1N aqueous NaOH (1 mL) was added under stirring at room temperature, and reacted at room temperature for 2 h. The reaction solution was concentrated under reduced pressure to remove MeOH, diluted with water, and then adjusted to pH2 with 1N HCl. The mixture was extracted with EA and washed with brine. The aqueous layer was back-extracted once and the organic phase was dried over $Na_2SO_4$, filtrated and concentrated. The obtained crude product was recrystallized from PE/DCM to give the product CLH680 (8.8 mg, 72%, white solid). $^1$H NMR (CDCl$_3$, 300 MHz): δ 7.57 (d, J=7.5 Hz, 2H), 7.20-7.40 (m, 6H), 6.90-7.15 (m, 8H), 3.44 (q, J=7.2 Hz, 2H), 1.24 (d, J=7.2 Hz, 6H).

The following compound was synthesized in the same manner:

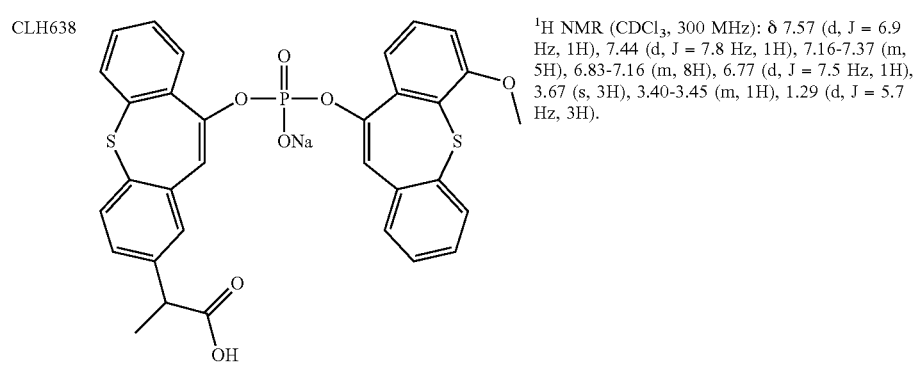

$^1$H NMR (CDCl$_3$, 300 MHz): δ 7.57 (d, J = 6.9 Hz, 1H), 7.44 (d, J = 7.8 Hz, 1H), 7.16-7.37 (m, 5H), 6.83-7.16 (m, 8H), 6.77 (d, J = 7.5 Hz, 1H), 3.67 (s, 3H), 3.40-3.45 (m, 1H), 1.29 (d, J = 5.7 Hz, 3H).

Example 6

Preparation of Compounds CLH600, CLH584 and CLH568a

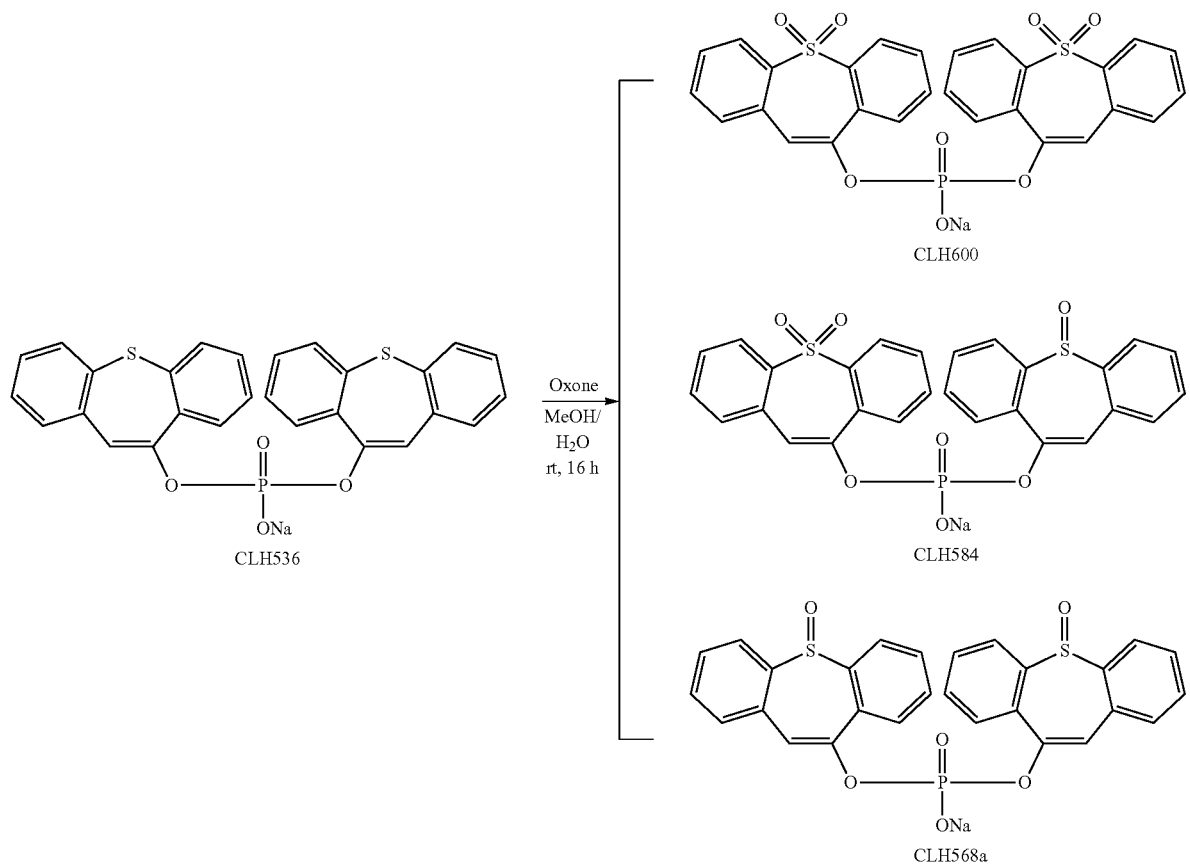

The starting material CLH536 (100 mg, 0.186 mmol) was dissolved in MeOH (20 mL). A solution of Oxone (potassium hydrogen peroxymonosulfate, 500 mg, 1.627 mmol) in H$_2$O was added dropwise under stirring at room temperature and reacted at room temperature overnight. The reaction solution was diluted with water, extracted with EA, washed with brine and subjected to silica gel column chromatography (DCM/MeOH=25/1-6/1) to obtain the products.

CLH600 (20 mg, 18%, white solid). $^1$H NMR (d$_6$-DMSO, 300 MHz): δ 8.16 (s, 2H), 8.06 (d, J=7.2 Hz, 4H), 7.65-7.80 (m, 8H), 7.50-7.65 (m, 4H).

CLH584 (12 mg, 11%, white solid). $^1$H NMR (d$_6$-DMSO, 300 MHz): δ 8.00-8.12 (m, 3H), 7.46-7.80 (m, 11H), 7.30-7.46 (m, 4H).

CLH568a (10 mg, 9%, white solid). $^1$H NMR (d$_6$-DMSO, 300 MHz): δ 6.60-7.90 (m, 8H), 7.56 (t, J=7.2 Hz, 2H), 7.32-7.50 (m, 7H), 7.25 (d, J=7.2 Hz, 1H).

Example 7

Preparation of Compound XYF532

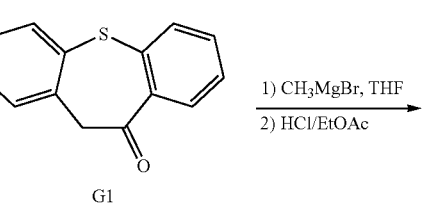

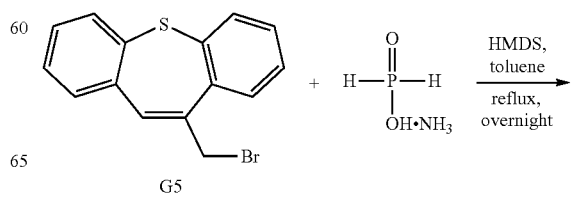

-continued

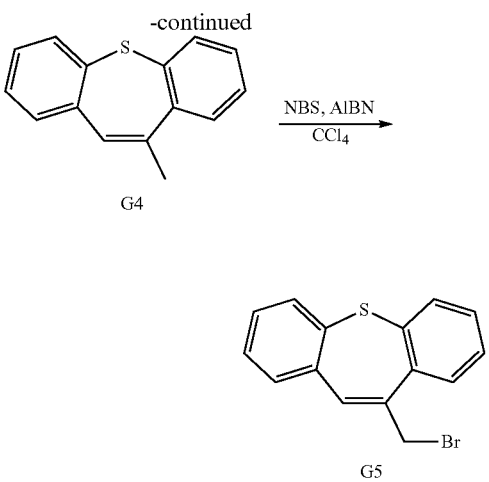

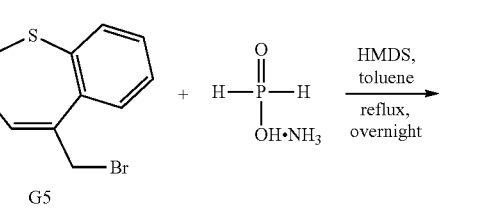

-continued

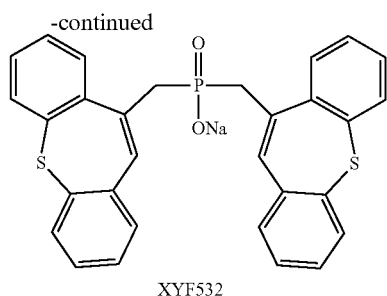

XYF532

The starting material G1 (226 mg, 1 mmol) was dissolved in THF (4 mL), and a solution of methylmagnesium bromide in diethyl ether (3 mol/L, 0.5 mL) was added dropwise under the ice bath, then warmed to room temperature and reacted for 3 hours. The saturated ammonium chloride solution was added to quench the reaction. The mixture was extracted with EA, washed with saturated brine, dried over anhydrous sodium sulfate and dried by rotary evaporation. A solution of hydrochloric acid/ethyl acetate solution (4 mol/L, 2 mL) was added and reacted at room temperature overnight. The reaction solution was concentrated and the crude product was separated by column chromatography (PE/EA=20/1-10/1) to afford product G4 (135 mg, yield 60%).

The starting material G4 (135 mg, 0.60 mmol) was dissolved in carbon tetrachloride (5 mL), and NBS (139 mg, 0.78 mmol) and AIBN (10 mg) were added successively, and the mixture was heated to reflux for 5 hours, then cooled to room temperature and filtered to remove the solid. The filtrate was concentrated and separated by column chromatography to afford product G5 (82 mg, yield 45%).

The starting material G5 (100 mg, 0.33 mmol) and amine phosphite (11 mg, 0.13 mmol) were dissolved in anhydrous toluene (1.5 mL), and hexamethyldisilazane (HMDS, 110 μL, 0.53 mmol) was added under argon atmosphere and heated to reflux overnight. The mixture was cooled to room temperature and dried by rotary evaporation to remove toluene. Then dichloromethane:methanol (1:1) was added to dissolve the residue. The mixture was dried by rotary evaporation and subjected to silica gel column chromatography (DCM/MeOH=25/1-6/1) to give product XYF 532 (30 mg, yield 43%). $^1$H NMR (CDCl$_3$, 300 MHz): δ 7.10-7.40 (m, 18H), 2.96-3.27 (br, 4H).

Example 8

1. Experiment Purpose

GPR84 antagonistic activity of the compounds of the invention was determined.

2. Material Source

The human GPR84 cell line was obtained by transfecting a HEK293 cell line with a plasmid encoding GPR84 and Gα16 proteins. Fluorescent dye Fluo-4AM was purchased from Invitrogen.

3. Test Principle

Intracellular Ca$^{2+}$ ion is a very important second messenger of G protein-coupled receptor signaling pathway. When combined with Gα16 protein-coupled GPR84 and agonist, intracellular Ca$^{2+}$ ion concentration can be significantly increased. Fluo-4 is a Ca$^{2+}$ ion-specific fluorescent probe that binds quantitatively to Ca$^{2+}$ ions and emits fluorescence. Therefore, the agonistic or antagonistic activity of the compound can be detected in a 96-well or 384-well flat-bottomed microplate using a fluorescence assay.

Detection of receptor inhibitory effect by GPR84 antagonist: After incubated with fluorescent dye Fluo-4, GPR84 cells were incubated with different concentrations of antagonistic compounds for a period of time to occupy the binding site of agonist to GPR84 (antagonistic binding site). A certain concentration of agonist (6-OAU) was added to compete with the antagonist compound for binding sites. A light source with a wavelength of 485 nm was used for excitation and changes in the fluorescence intensity of the dye caused by changes in intracellular calcium concentration at 525 nm was detected. The half-inhibitory concentration (IC$_{50}$) of the compound was calculated by using GraphPad PRISM software.

4. Experiment Procedure

Preparation of HBSS: 0.4 g/L KCl (5.4 mM), 0.12 g/L Na$_2$H PO$_4$.12H$_2$O (0.3 mM), 0.06 g/L KH$_2$PO$_4$ (0.4 mM), 0.35 g/L NaHCO$_3$ (4.2 mM), 0.14 g/L CaCl$_2$) (1.3 mM), 0.10 g/L MgCl$_2$.6H$_2$O (0.5 mM), 0.05 g/L MgSO$_4$ (0.6 mM), 8.0 g/L NaCl (137 mM). The above ingredients were weighed and dissolved in ultrapure water. pH was adjusted to 7.4 by using hydrochloric acid or NaOH solution. The mixture was filtered and stored at 4° C. for one month.

Preparation of calcium buffer: 560 mM D-glucose (100×) aqueous stock solution and 250 mM 1,2-diphenyl-4-(2-phenylsulfinyl)ethyl-3,5-pyrazolidinedione (1000×) stock solution were firstly prepared. Then BSA (0.5 g), 560 mM D-glucose (1 mL) stock solution and 250 mM 1,2-diphenyl-4-(2-phenyl sulfinyl)ethyl-3,5-pyrazolidinedione (100 μL) stock solution were added to 100 mL HBSS to a final concentration of 0.5% BSA, 5.6 mM D-glucose, 250 μM 1,2-diphenyl-4-(2-phenylsulfinyl)ethyl-3,5-pyrazolidinedione and mixed. The buffer was prepared on site.

Preparation of dyes: 3% Cremophor EL (100×) stock solution in PBS and 2 mM Fluo-4 (1000×) stock solution in DMSO were firstly prepared. The preparation of each milliliter of dye is as follows. 1 μL of 2 mM Fluo-4 AM was mixed with 10 μL of 3% Cremophor EL, then diluted with 1 mL of calcium buffer and mixed.

The cells were seeded at a density of 40,000 cells/well into a 96-well cell culture plate, and cultured for 24 hours or more to a cell density of 80 to 90% for experimental detection. The culture medium in the well to be tested was removed and 40 μL/well of freshly prepared dye was added and incubated in a 37-degree incubator for 40 min to 50 min.

The compound was formulated during cell incubation (this step can also be carried out in advance). The compound used as antagonist was diluted with calcium buffer freshly prepared before the experiment to 1.5 times of the final working concentration. The compound as agonist was diluted to 3 times of the final working concentration (if the compound is dissolved in DMSO, the final work concentration of DMSO shall not exceed 1%).

After the incubation step was completed, the dye was discarded, and the residue was washed with calcium buffer once and then replaced with 50 μL of calcium buffer containing different concentrations of antagonist and incubated for another 10 min.

25 μL/well of calcium buffer containing a certain concentration of agonist (usually an effective concentration of agonist EC$_{50}$) was added for stimulation and a light source with a wavelength of 485 nm was used for excitation and changes in the fluorescence intensity of the dye caused by changes in intracellular calcium concentration at 525 nm was detected by using a FlexStation III microplate reader.

5. Experiment Results

TABLE 1

IC$_{50}$ of the compound detected by the GPR84 calcium flow model

| Compound No. | GPR84 |
|---|---|
| CLH472 | * |
| CLH472a | ** |
| CLH478 | *** |
| CLH482 | ** |
| CLH508 | ** |
| CLH514 | *** |
| CLH524 | ** |
| CLH524a | ** |
| CLH528 | ** |
| CLH528a | ** |
| XYF528 | ** |
| XYF532 | * |
| CLH536 | *** |
| CLH544 | ** |
| CLH544a | ** |
| CLH548 | *** |
| CLH552 | *** |
| CLH560 | *** |
| XYF560 | ** |
| XYF604b | *** |
| XYF604c | *** |
| XYF540 | *** |
| CLH568 | *** |
| CLH572a | ** |
| CLH572b | ** |
| CLH572c | ** |
| XYF573 | ** |
| XYF573a | ** |
| XYF573b | *** |
| XYF573c | *** |
| CLH582 | *** |
| CLH584 | * |
| CLH596a | *** |
| CLH596b | *** |
| CLH596c | *** |
| CLH600 | * |
| XYF608 | *** |
| CLH616a | ** |
| CLH624 | *** |
| XYF628 | * |
| XYF628a | *** |
| XYF564b | *** |
| XYF564c | *** |
| XYF628b | ** |
| XYF628c | *** |
| XYF632 | *** |
| XYF632a | *** |
| XYF632b | *** |
| XYF632c | *** |
| CLH638 | *** |
| CLH652 | ** |
| CLH656 | *** |
| CLH656a | ** |
| XYF656 | *** |
| XYF656a | ** |
| XYF656b | *** |
| CLH666 | *** |
| CLH680 | * |
| CLH736 | * |
| XYF536c | *** |
| XYF604 | ** |
| XYF604a | ** |
| XYF564-2a | *** |
| XYF564a | *** |

\* 1-10 μM;
\*\* 0.1-1 μM;
\*\*\* 0.1-100 nM

All documents mentioned in the present application are incorporated herein by reference, just as each document is cited separately as a reference. In addition, it should be understood that various modifications and changes may be made by those skilled in the art after reading the above teachings of the present invention. These equivalent forms are also within the scope defined by the claims appended hereto.

The invention claimed is:

1. A compound or a pharmaceutically acceptable salt having the structure of formula I,

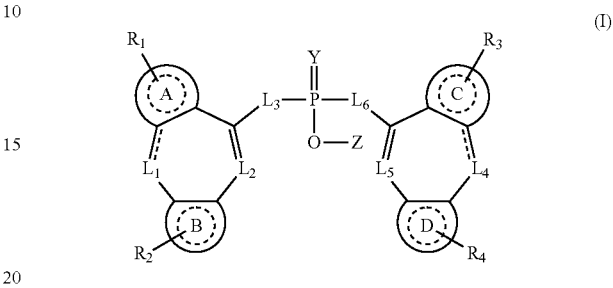

wherein,

Y is O or S;

Z is H, or an ion of the following metal: $L_1$, Na, K, Ca, Mg, Cu, Fe, Zn, Al, Mn, or a conjugated acid of the following base: NH$_3$, arginine, betaine, caffeine, choline, N,N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, glucosamine, aminoglucose, histidine, hydroxycobalamin, isopropylamine, lysine, methyl glucosamine, morpholine, piperazine, piperidine, polyamine resin, procaine, purine, theobromine, triethylamine, trimethylamine, tripropylamine, trometamol;

$L_3$ and $L_6$ are each O;

each of rings A, B, C, and D is independently a benzene ring or a thiophene ring;

$R_1$, $R_2$, $R_3$, and $R_4$ are each independently 1 to 4 substituents on rings A, B, C, and D, and each substituent is independently absent, hydroxyl, mercapto, amino, F, Cl, Br, I, —C$_r$H$_{2r}$-L$_7$-C$_s$H$_{2s+1}$, —C$_r$H$_{2r}$—N(C$_t$H$_{2t+1}$)—C$_s$H$_{2s+1}$, substituted or unsubstituted C$_1$-C$_6$ alkyl, the above substitution means there is one or more substituents selected from the group consisting of C$_1$-C$_6$ alkyl, C$_1$-C$_6$ alkoxy, halogen, hydroxyl, amino, —COOC$_1$-C$_6$ alkyl, —COOH; $L_7$ is each independently O, S, NH, each r is independently an integer of 0-6, each s is independently an integer of 0-6, and each t is independently an integer of 1-6;

$L_2$ and $L_5$ are each independently absent or CH;

$L_1$ and $L_4$ are each independently absent, CH, O, S, SO, SO$_2$, —CH=CH—, CO, —C(=CH$_2$)—, substituted or unsubstituted C$_1$-C$_6$ alkylidene, —NH—, —N(C$_1$-C$_4$ alkyl)-, said "substituted" means that there is one or more substituents selected from the group consisting of C$_1$-C$_6$ alkyl, C$_1$-C$_6$ alkoxy, halogen, hydroxy;

---- represents a single bond or a double bond.

2. The compound according to claim 1, wherein $R_1$, $R_2$, $R_3$ and $R_4$ are each independently one, two or three substituents on rings A, B, C and D, and each substituent is independently absent, substituted or unsubstituted C$_1$-C$_4$ alkyl, —C$_r$H$_{2r}$-L$_7$-C$_s$H$_{2s+1}$, —C$_r$H$_{2r}$—N(C$_t$H$_{2t+1}$)—C$_s$H$_{2s+1}$, hydroxyl, mercapto, amino, F, Cl, Br, I; the above substitution means there is one or more substituents selected from the group consisting of halogen, hydroxyl, amino, —COOC$_1$-C$_6$ alkyl, —COOH; $L_7$ is each independently O, S, NH, each r is independently an integer of 0-4, each s is independently an integer of 0-4, and each t is independently an integer of 1-4.

3. The compound according to claim 1, wherein $L_1$ and $L_4$ are each independently absent, CH, O, S, SO, $SO_2$, —CH=CH—, CO, —C(=$CH_2$)—, substituted or unsubstituted $C_1$-$C_4$ alkylidene, —NH—, —N($C_1$-$C_3$ alkyl)-, $C_3$-$C_6$ cycloalkyl or $C_3$-$C_6$ oxa-cycloalkyl, said substitution means there is one or more substituents selected from the group consisting of $C_1$-$C_6$ alkyl, $C_1$-$C_6$ alkoxy, halogen, hydroxyl.

4. The compound according to claim 1, wherein, a carbon attached to $L_3$ and/or $L_6$ and a carbon of ring B and/or ring D form —CH=CH— when $L_2$ and/or $L_5$ are absent;

a carbon attached to $L_3$ and/or $L_6$ and a carbon attached to $L_2$ and/or $L_5$ form —CH=CH when $L_2$ and/or $L_5$ are CH.

5. A compound having the following structure

CLH472
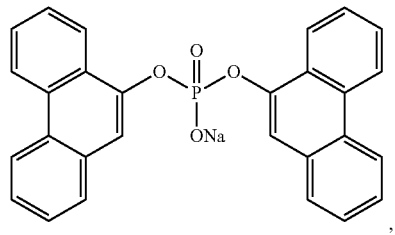

CLH472a
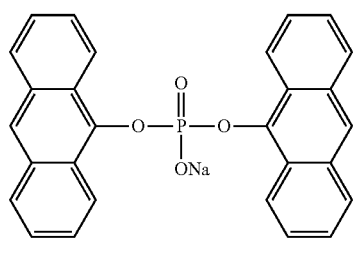

CLH478
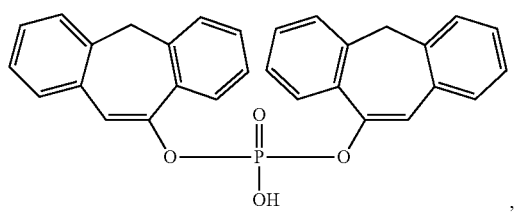

CLH482
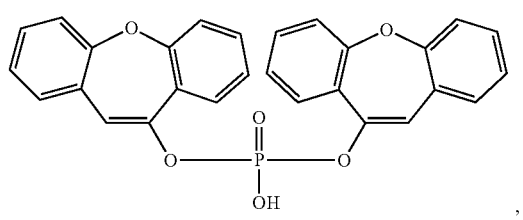

-continued

CLH508
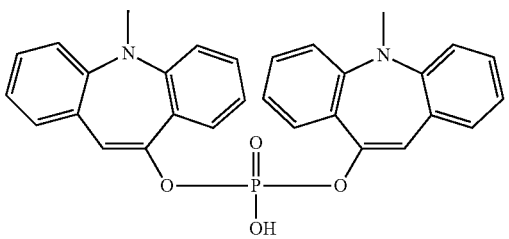

CLH514
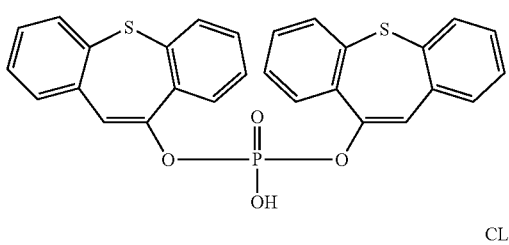

CLH524
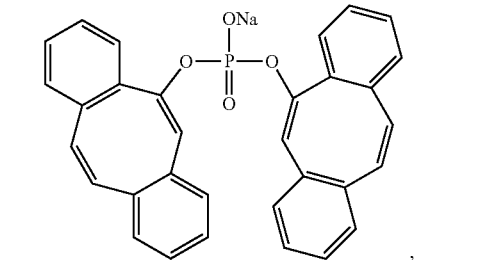

CLH524a
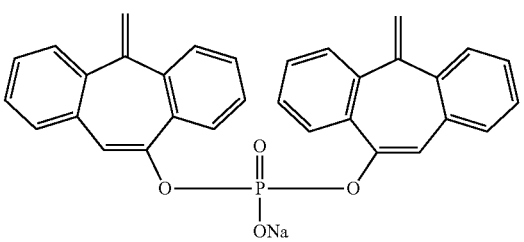

CLH528
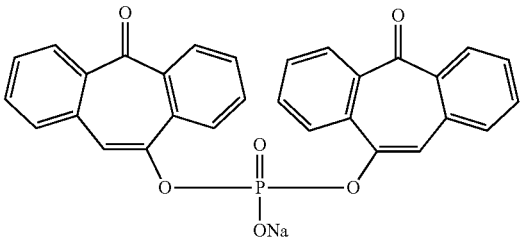

CLH528a
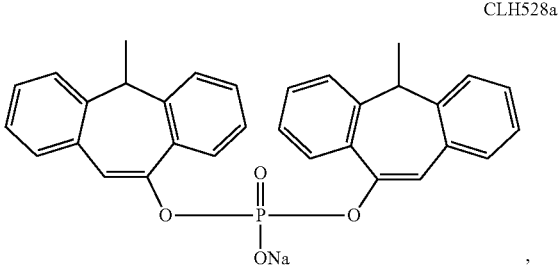

XYF528
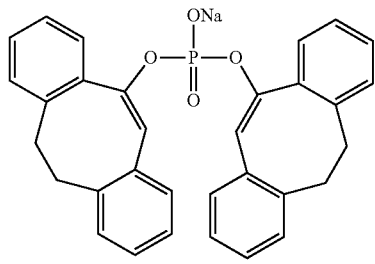
CLH552
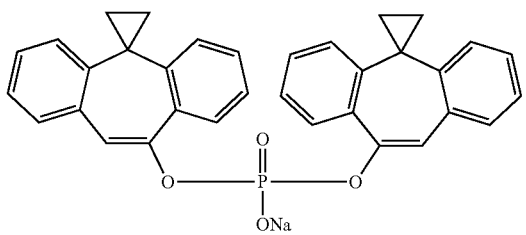
XYF532
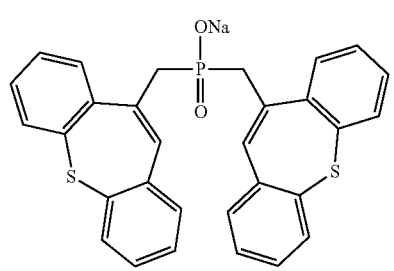
CLH560
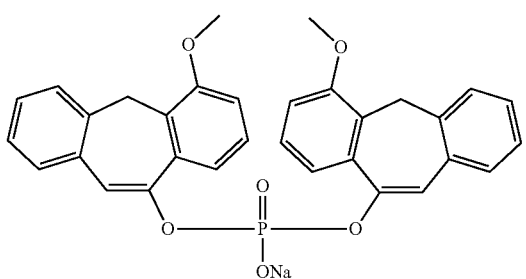
CLH536
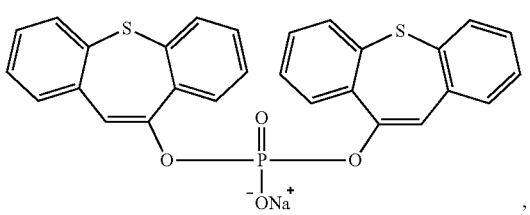
XYF560
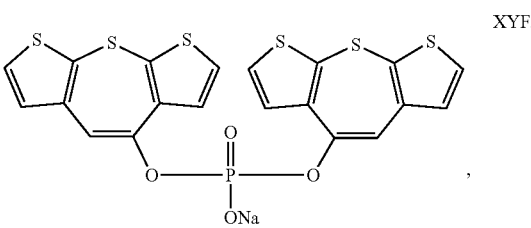
CLH544
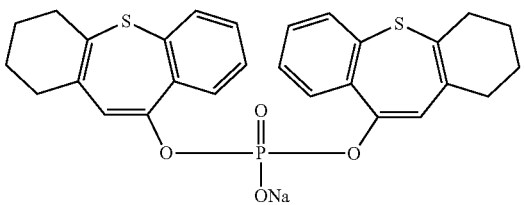
CLH568
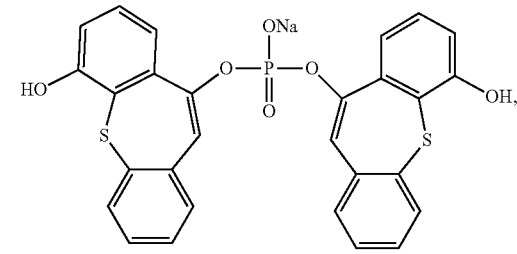
CLH 544a
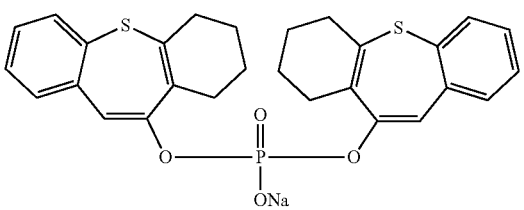
CLH568a
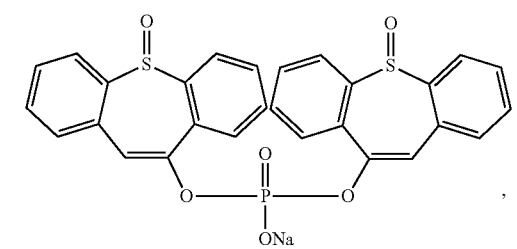
CLH548
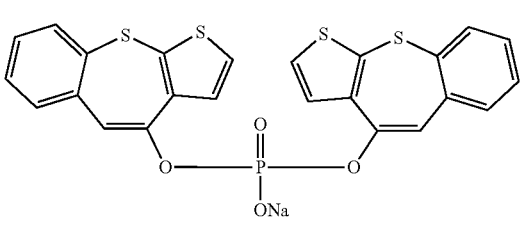
CLH527a
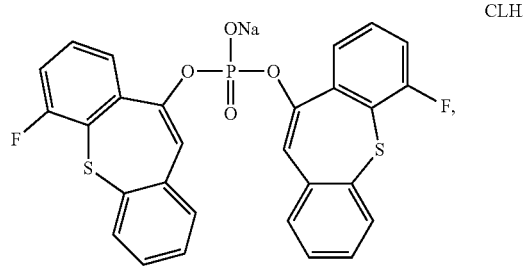

-continued
CLH572b
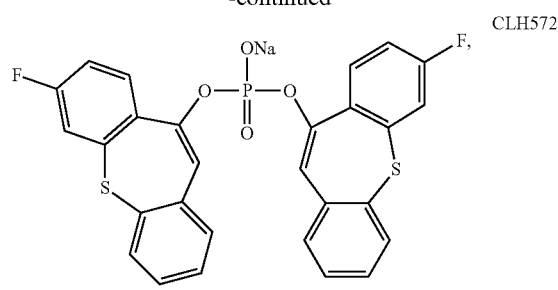
XYF573c
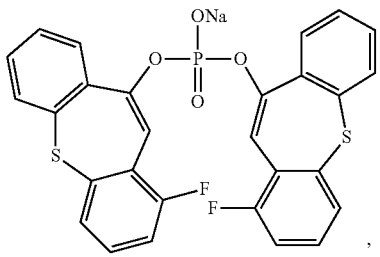
CLH572c
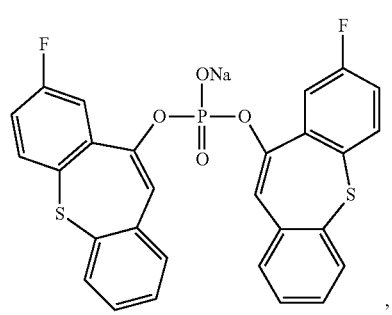
CLH582
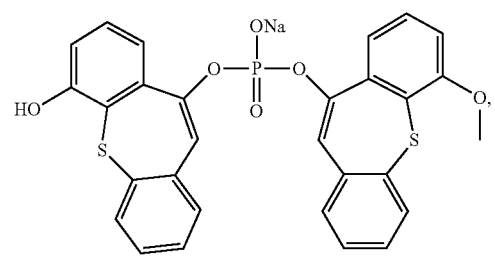
XYF573
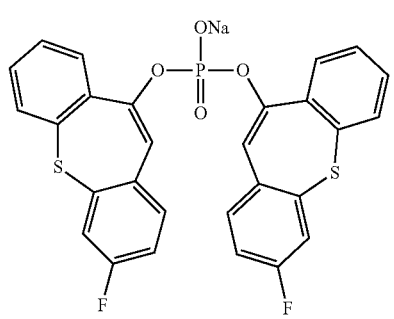
CLH584
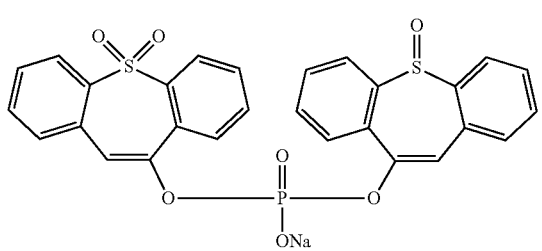
XYF573a
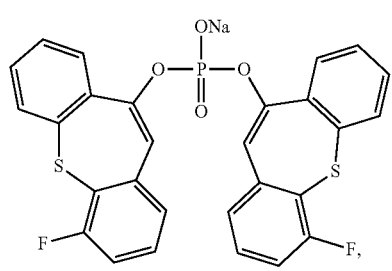
CLH596a
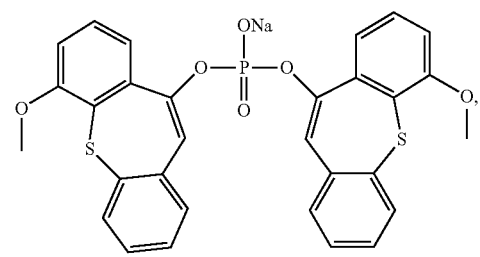
XYF573b
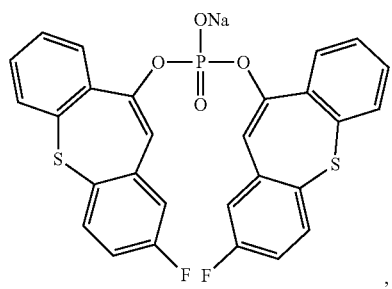
CLH596b
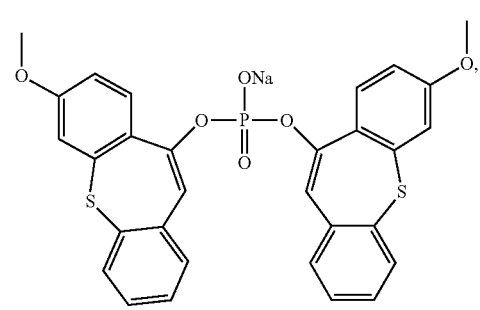

CLH596c
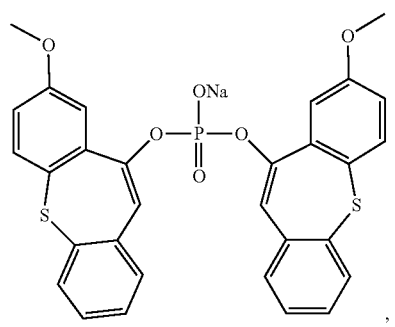
CLH600
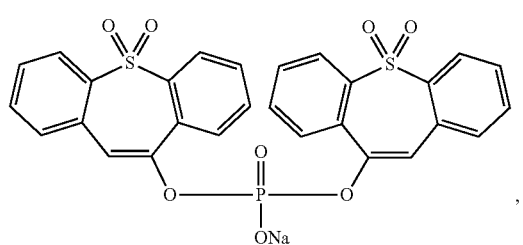
XYF608
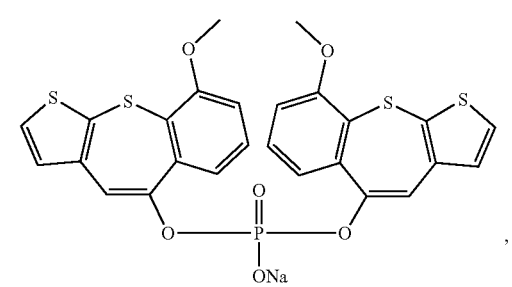
CLH616a
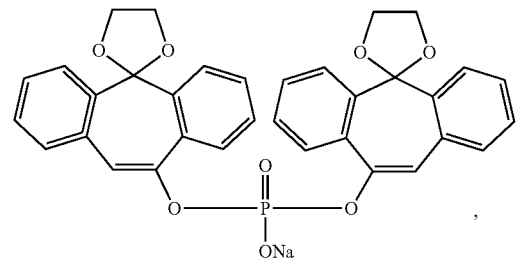
CLH624
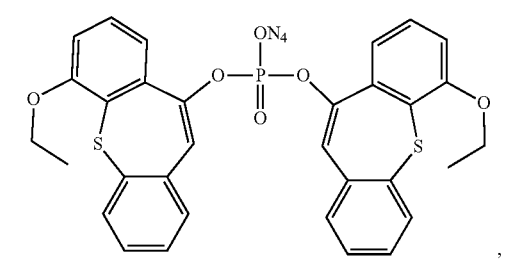
XYF628
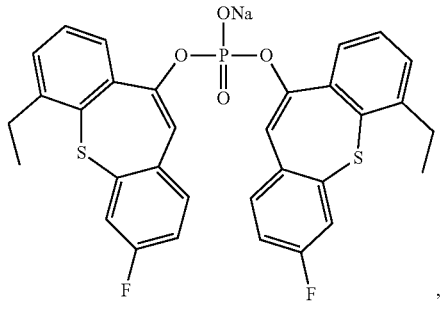
XYF628a
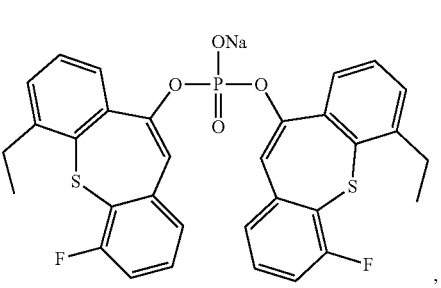
XYF628b
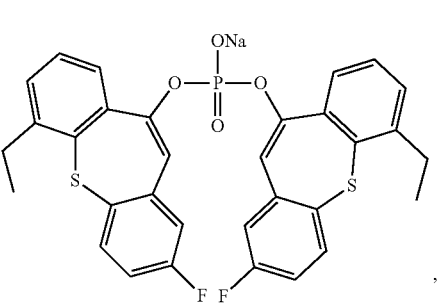
XYF628c
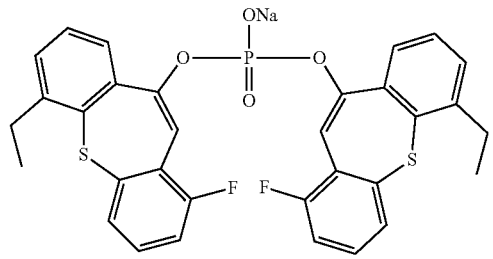
XYF632
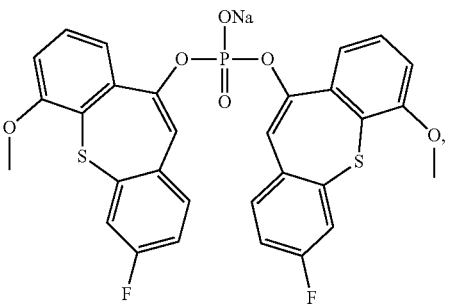

-continued
XYF632a
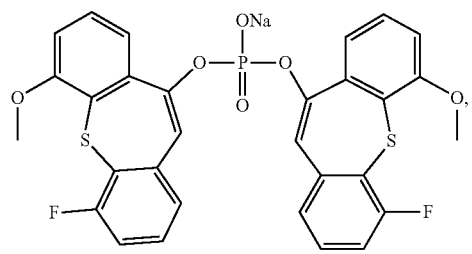
XYF632b
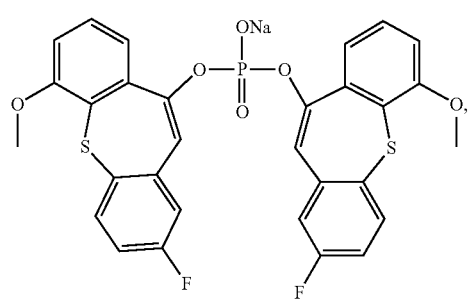
XYF632c
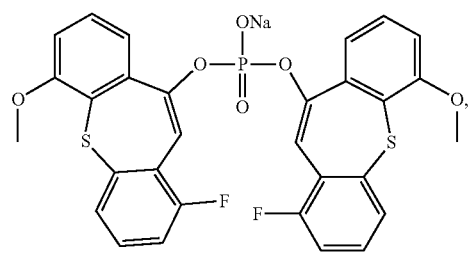
CLH652
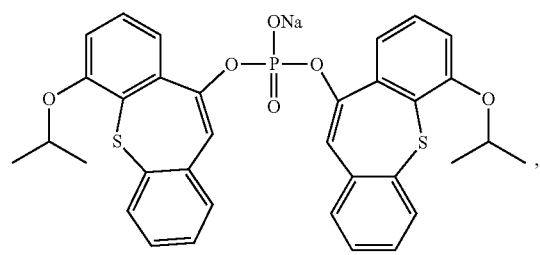
CLH638
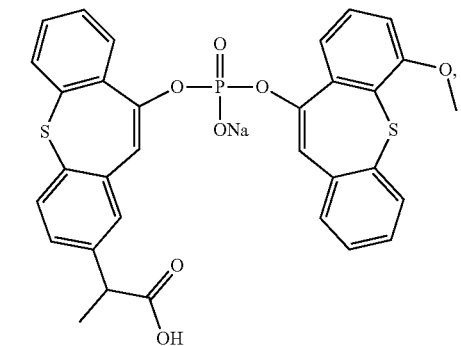
-continued
CLH656
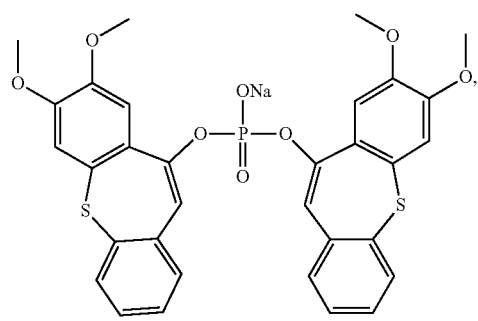
CLH656a
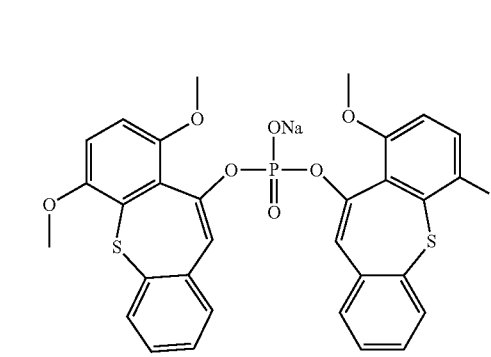
XFY656
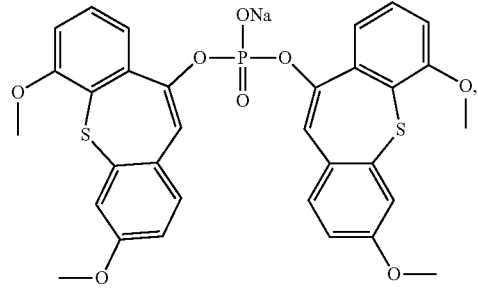
XYF656a
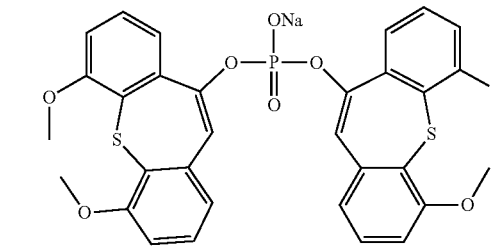
XYF656b
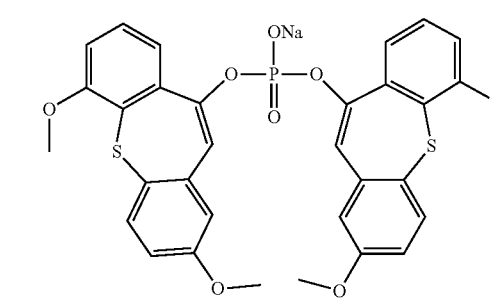

CLH666
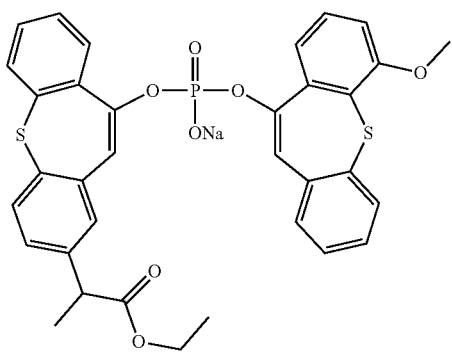
CLH680
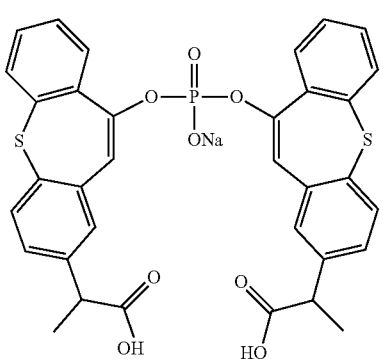
CLH736
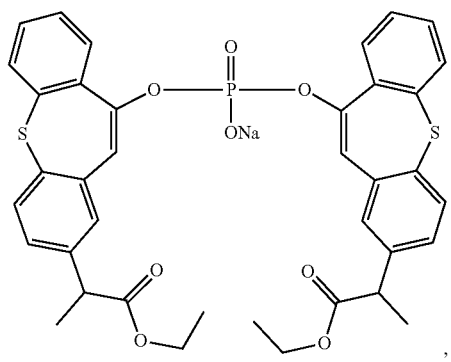
XYF563c
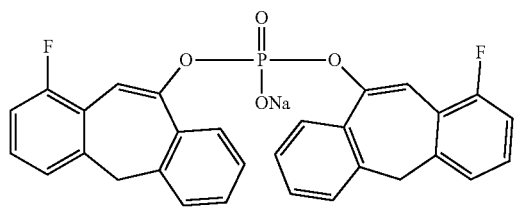
XYF604
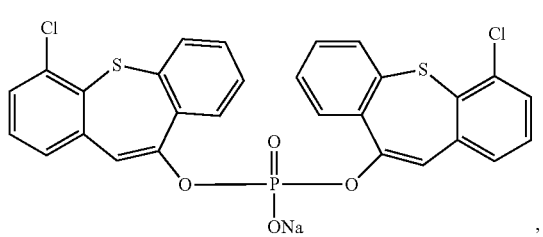
XYF604a
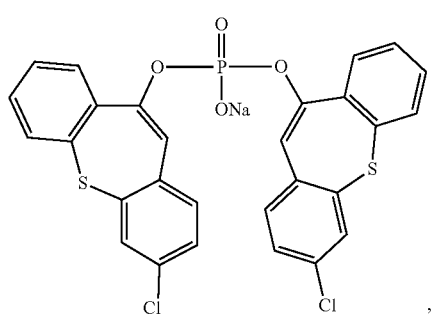
XYF604b
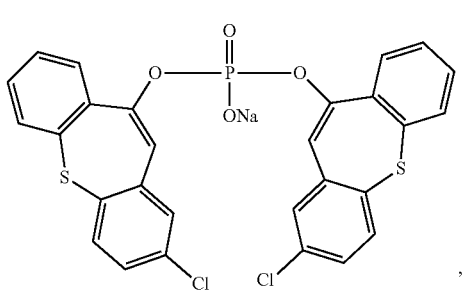
XYF604c
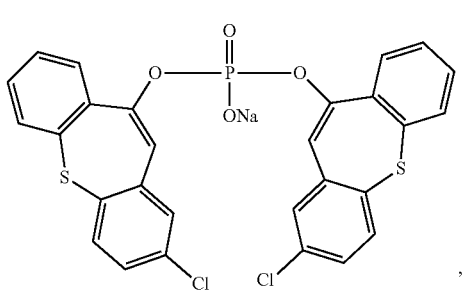
XYF564a
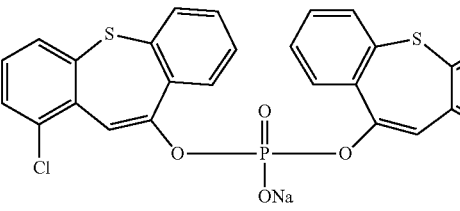
XYF564b
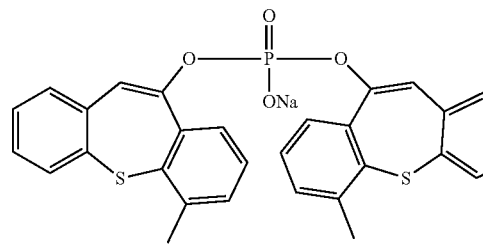
XYF564c
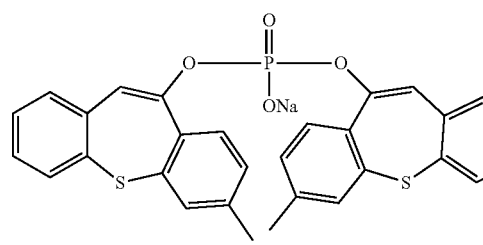
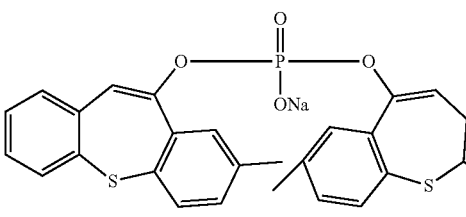

-continued

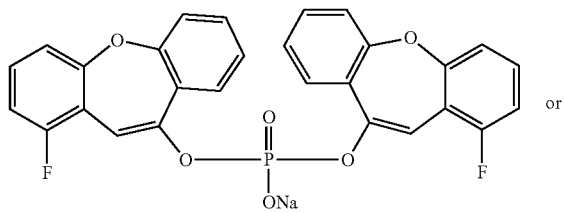
XYF540

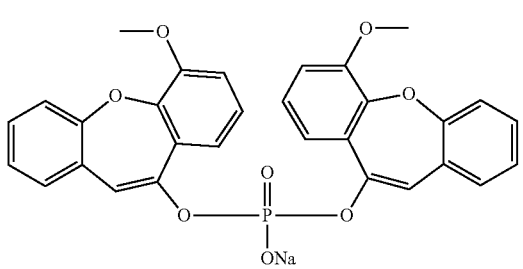
XYF564-2a

6. A method for preparing the compound according to claim 1, wherein the method comprises the following step:

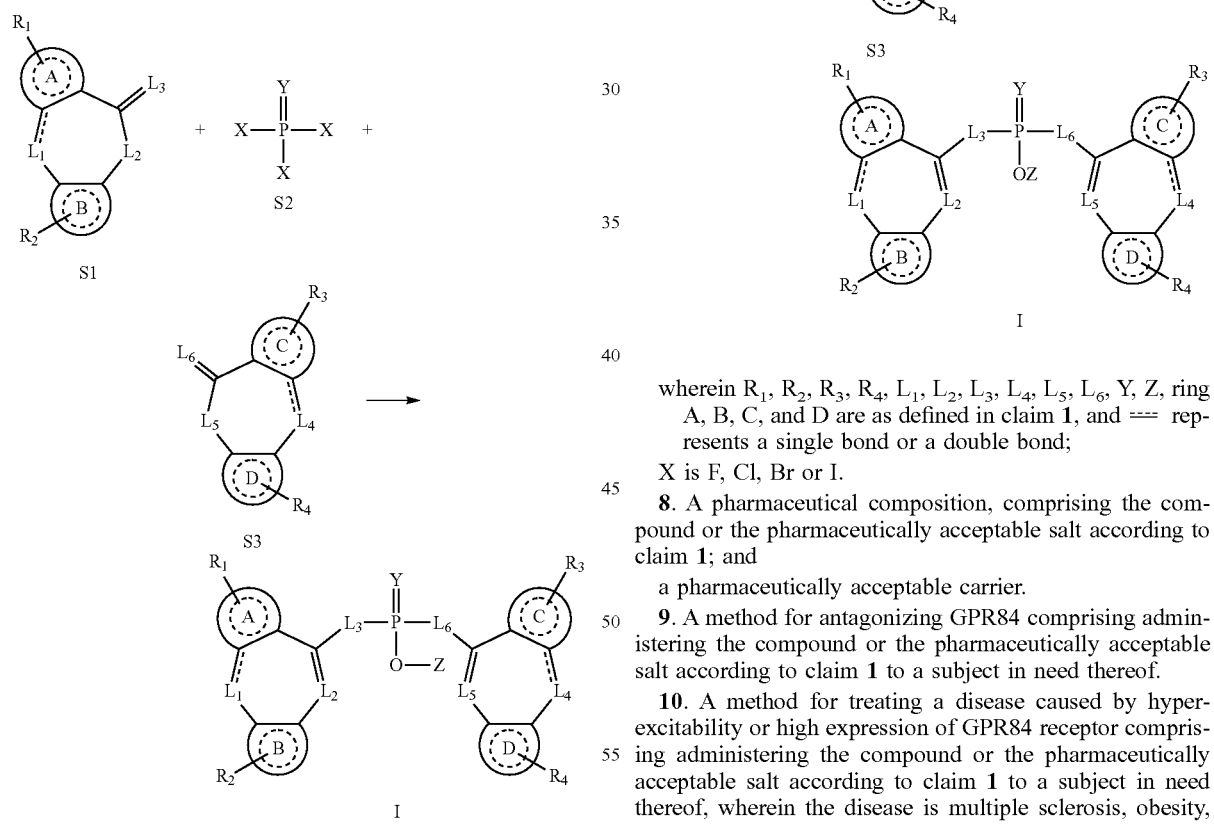

reacting a compound of formula S1, a compound of formula S2 and a compound of formula S3 as starting materials to obtain the compound of formula I, wherein $R_1$, $R_2$, $R_3$, $R_4$, $L_1$, $L_2$, $L_3$, $L_4$, $L_5$, $L_6$, Y, Z, ring A, B, C, and D are as defined in claim 1, and ≡≡≡ represents a single bond or a double bond;

X is F, Cl, Br or I.

7. A method for preparing the compound according to claim 1, wherein the method comprises the following steps:

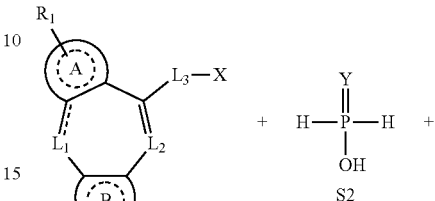

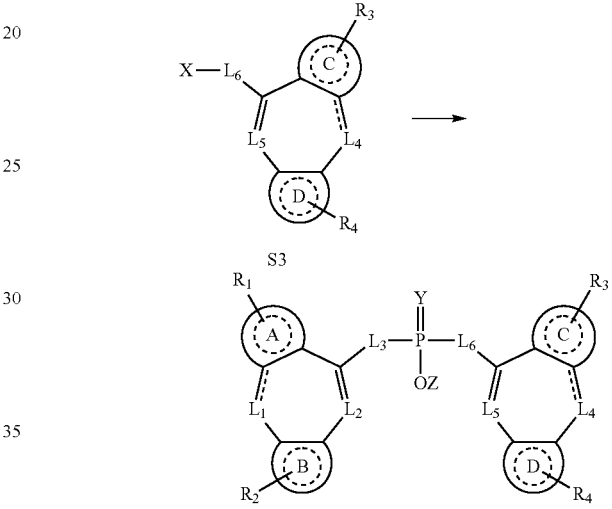

wherein $R_1$, $R_2$, $R_3$, $R_4$, $L_1$, $L_2$, $L_3$, $L_4$, $L_5$, $L_6$, Y, Z, ring A, B, C, and D are as defined in claim 1, and ≡≡≡ represents a single bond or a double bond;

X is F, Cl, Br or I.

8. A pharmaceutical composition, comprising the compound or the pharmaceutically acceptable salt according to claim 1; and a pharmaceutically acceptable carrier.

9. A method for antagonizing GPR84 comprising administering the compound or the pharmaceutically acceptable salt according to claim 1 to a subject in need thereof.

10. A method for treating a disease caused by hyperexcitability or high expression of GPR84 receptor comprising administering the compound or the pharmaceutically acceptable salt according to claim 1 to a subject in need thereof, wherein the disease is multiple sclerosis, obesity, inflammatory bowel disease or arthritis.

11. The method of claim 10, wherein the disease is multiple sclerosis, inflammatory bowel disease or arthritis.

* * * * *